(12) United States Patent
Nossner et al.

(10) Patent No.: US 6,903,080 B2
(45) Date of Patent: Jun. 7, 2005

(54) DISEASE TREATMENT WITH NOVEL PHOSPHOLIPID DERIVATIVES

(75) Inventors: Gerhard Nossner, Feucht (DE); Bernhard Kutscher, Maintal (DE); Jurgen Engel, Alzenau (DE); Wolfgang Schumacher, Langen (DE); Jurij Stekar, deceased, late of Bielefeld (DE); by Margrit Stekar, legal representative, Bielefeld (DE); Peter Hilgard, Frankfurt am Main (DE)

(73) Assignee: Zentaris GmbH, Frankfurt (DE)

( * ) Notice: Subject to any disclaimer, the term of this patent is extended or adjusted under 35 U.S.C. 154(b) by 49 days.

(21) Appl. No.: 10/290,436

(22) Filed: Nov. 8, 2002

(65) Prior Publication Data

US 2003/0153533 A1 Aug. 14, 2003

(Under 37 CFR 1.47)

Related U.S. Application Data

(60) Division of application No. 09/672,497, filed on Sep. 29, 2000, now Pat. No. 6,479,472, which is a division of application No. 08/905,333, filed on Aug. 4, 1997, now Pat. No. 6,172,050, which is a continuation of application No. 08/487,624, filed on Jun. 7, 1995, now abandoned, which is a continuation-in-part of application No. 08/086,850, filed on Jul. 7, 1993, now abandoned.

(30) Foreign Application Priority Data

Jul. 11, 1992 (DE) .......................................... P4222910

(51) Int. Cl.$^7$ .................... A61K 31/661; A61K 31/662; A61P 35/00
(52) U.S. Cl. ........................................ 514/89; 514/114
(58) Field of Search ................... 514/89, 114; 544/337; 558/169, 176

(56) References Cited

U.S. PATENT DOCUMENTS

| | | | | |
|---|---|---|---|---|
| 4,444,766 A | 4/1984 | Bosies et al. | ............... | 424/211 |
| 4,542,219 A | 9/1985 | Huzumi | ............... | 546/22 |
| 4,778,788 A | 10/1988 | Munder | ............... | 514/77 |
| 4,935,520 A | 6/1990 | Najima | ............... | 546/22 |
| 5,049,552 A | 9/1991 | Eibl | ............... | 514/77 |
| 5,053,402 A | 10/1991 | Masaki | ............... | 514/79 |
| 5,183,811 A | 2/1993 | Masaki | ............... | 514/79 |

FOREIGN PATENT DOCUMENTS

| | | |
|---|---|---|
| CA | 2011209 | 4/1990 |
| DE | 35 30 767 | 3/1987 |
| DE | 36 41 379 | 9/1987 |
| DE | 39 06 952 | 9/1990 |
| DE | 39 42 933 | 6/1991 |
| DE | 41 14 586 | 11/1992 |
| SU | 1241994 | 6/1986 |
| SU | 1376948 | 2/1988 |

OTHER PUBLICATIONS

E Aboud–Pirak, E Hurwitz, F Bellot, J Schlessinger, and M Sela, Proc Natl Acad Sci U S A. May 1989; 86 (10): 3778–3781.*
P. Hilgard, T. Klenner, J. Stekar, G. Nössner, B. Kutscher and J. Engel, European Journal of Cancer vol. 33, Issue 3, Mar. 1997, pp. 442–446.*
Polman, C.H. et al, BMJ 2000, 321, 490–4.*
Cohen, J.A. et al, J. Neuroimmun., 1999, 98 29–36.*
Yanapirut, et al., "In vitro Investigations on the Antineoplastic Effect of Hexadecylphosphocholine," *Arzneim.–Forsch./Drug Res.*, 41 (1), No. 6, 1991, pp. 652–655.
Isselbachen et al., *Harrison's Principles of Internal Medicine*, 13$^{th}$ ed. (1994), vol. 2, pp. 1826–1829.
Wyngaarden et al., *Cecil Textbook of Medicine*, 19$^{th}$ ed. (1992), pp. 1049–1053.
Berkow et al., *The Merck Manual*, 15$^{th}$ Ed. (1987), pp. 1226–1227.
Polman et al., *BMJ2000*, vol. 321, pp. 490–494.
Cohen et al., *J. Neuroimmun.*, vol. 98, 1999, pp. 29–36.
Fields et al., *Fields Virology*, vol. 1, 3$^{rd}$ Ed., 1996, p. 431.
Hawley, *The Condensed Chemical Dictionary*, 9$^{th}$ Ed., 1977, pp. 27 and 650.

* cited by examiner

*Primary Examiner*—James O. Wilson
*Assistant Examiner*—Thomas C. McKenzie
(74) *Attorney, Agent, or Firm*—Pillsbury Winthrop LLP

(57) ABSTRACT

A method of treating protozoal and fungal diseases is described, in which an effective amount of a compound of formula I is administered to a host having a protozoal or fungal disease. Also described are methods of treating bone marrow damage composed of administering, to a host having bone marrow damage due to treatment with cytostatic agents or other myelotoxic active ingredients, an effective amount of a compound of formula I $$R-X-A-\underset{\underset{O^-}{|}}{\overset{\overset{O}{\|}}{P}}O(CH_2)_y-CH\underset{(CH_2)_n}{\overset{(CH_2)_m}{<}}\overset{+}{N}\underset{R^2}{\overset{R^1}{<}} \quad (I)$$

3 Claims, 17 Drawing Sheets

DISEASE TREATMENT WITH NOVEL PHOSPHOLIPID DERIVATIVES

This is a divisional of application Ser. No. 09/672,497, filed Sep. 29, 2000, now U.S. Pat. No. 6,479,472, which is a divisional of application Ser. No. 08/905,333, filed Aug. 4, 1997, now U.S. Pat. No. 6,172,050, which is a continuation of application Ser. No. 08/487,624, filed Jun. 7, 1995, now abandoned, which is a continuation-in-part of application Ser. No. 08/086,850, filed Jul. 7, 1993, now abandoned, which claims priority to German Application No. P 42 22 910.3, filed Jul. 11, 1992.

BACKGROUND OF THE INVENTION

Published European Patent Application 108 565 relates to compounds of the General Formula:

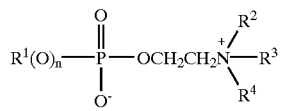

and their pharmaceutically acceptable salts, in which $R^1$ is an aliphatic hydrocarbon radical having 8–30 carbon atoms and the radicals $R^2$, $R^3$ and $R^4$ are identical or different and are hydrogen or lower alkyl radicals, or in which the group $NR^2R^3R^4$ is a cyclic ammonium group, and n has the value 0 or 1. Antitumor and antifungal activity are indicated for these compounds.

SUMMARY OF THE INVENTION

The present invention relates to alkyl or alkene phosphates in which the choline radical is part of a heterocyclic ring, to a process for the preparation of the class of compounds, to pharmaceutical compositions containing the compounds as active ingredients and to processes for the preparation of said drugs.

More specifically, the present invention provides compounds of the General Formula I:

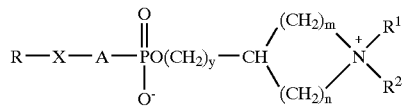

(I) next to the structure
in which
R is a linear or branched alkyl radical having 10 to 24 carbon atoms, which can also contain one to three double or triple bonds, $R^1$ and $R^2$ independently of one another are hydrogen or in each case a linear, branched or cyclic saturated or unsaturated alkyl radical having 1 to 6 carbon atoms, which can also contain a Cl, OH or $NH_2$ group, it also being possible for two of these radicals to be bonded together to form a ring,
A is a single bond or one of the groups of the formulae

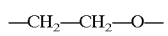                              (II)

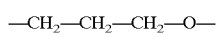                              (III)

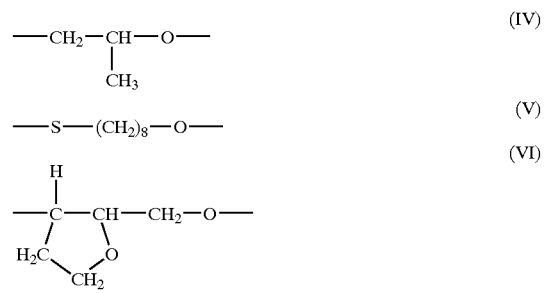

the groups (II) to (VI) being orientated in such a way that the oxygen atom is bonded to the phosphorus atom of compound (I), X is an oxygen or sulphur atom or NH when A is a single bond, or an oxygen or sulphur atom when A is one of the groups (II) to (IV),
y is equal to 0 or a natural number between 1 and 3, and m and n independently of one another are 0 or natural numbers, with the proviso that m+n=2 to 8.

The present invention also provides a pharmaceutical composition comprising, as the active ingredient, at least one compound according to General Formula (I) or a pharmaceutically acceptable salt thereof and a pharmaceutically acceptable carrier therefore. The pharmaceutical composition may also include pharmaceutically acceptable excipients, adjuncts, fillers and diluents. The amount of active ingredient in the pharmaceutical dosage unit the pharmaceutical composition is preferably between 50 mg and 250 mg. Preferred compounds for the pharmaceutical composition are selected from the group consisting of octadecyl 1,1-dimethylpiperidinio-4-yl phosphate, octadecyl 1,1-dimethylperhydroazepinio-4-yl phosphate, octaecyl 1,1-dimethylperhydroazepinio-4-yl phosphate, erucyl 1,1-dimethylpiperidinio-4yl phostphate and erucyl 1,1-dimethylperhydroazepinio-4-yl phosphate.

The present invention also provides methods of treating a tumor, autoimmune disease or skin disease or skin disease, and of combating protozoal and fungal diseases, which comprises administering to a host in need o such treatment an effective amount of a compound of General Formula (I). Such methods are particularly useful for treating leishmaniasis, multiple sclerosis, and psoriasis.

In addition, the invention provides a method of treating bone marrow damage due to treatment with cytostatic agents and other myeloxtoxic active ingredients which comprises administering, to a host having bone marrow damage due to treatment with cytostatic agents or other myelotoxic active ingredients, an effective amount of a compound of General Formula (I).

The invention also provides a method of treating a viral disease which comprises administering to a host having such a disease an effective amount of a compound of General Formula (I). This method should be particularly useful in treating AIDS.

Surprisingly, the compounds according to the invention have better antitumor activity than the open-chain derivatives described in EP-A 108 565. The invention further relates to processes for the preparation and processes for the purification of the novel compounds.

More specifically, the present invention relates to a procedure for the preparation of compounds of general formula I—further referred to as process A—in which a compound of the general formula VII described above in which a compound of the general formula in which R, X and A are as defined above, is reacted with phosphorus oxytrichloride in the presence of a suitable auxiliary base, with or without a solvent, and then reacted with a compound of the general formula:

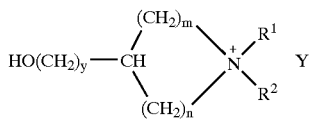

in which $R_1$, $R_2$, y, m and n are as defined above and Y is halide, mesylate or tosylate, to give compounds of the general formula I, or optionally compounds of the General Formula IX:

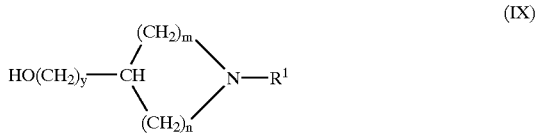

(IX)

in which $R_1$, y, m and n as defined above can be used instead of compounds of the general formula VIII during the process mentioned above. Process B consists in the subsequent alkylation of compounds of general formula I obtained by process A, in which $R_1$ and/or $R_2$ are hydrogen, using alkylating agents $R_2$-Y in which $R_2$ is as defined above and Y is chlorine, bromine, iodine, tosyl or mesyl, in a manner known per se.

The present invention also provides a process for the purification of the compounds of General Formula I in which a solution of the compounds of General Formula I, which have been prepared by means of known processes or by a process as described above, in an organic solvent is treated with a mixed bed ion exchanger or successively or simultaneously with an acid or basic ion exchanger.

The first step of process A consists in reacting phosphorus oxytrichloride with a compound of Formula VII in halogenated hydrocarbons, saturated cyclic ethers, acyclic ethers, saturated hydrocarbons having 5 to 10 carbon atoms or liquid aromatic hydrocarbons which can also be substituted by halogen (especially chlorine), or in mixtures of the above-mentioned solvents, or without a solvent, optionally in the presence of a basic substance conventionally used for this purpose.

Examples of possible halogenated hydrocarbons are hydrocarbons having 1 to 6 carbon atoms, one or more or all of the hydrogen atoms being replaced with chlorine atoms. Methylene chloride, chloroform, ethylene chloride, chlorobenzene and dichlorobenzene, for example, can be used. In the case of halogen-substituted aromatic hydrocarbons, these are preferably substituted by one or two halogen atoms.

Examples of saturated cyclic ethers which can be used are ethers with a ring size of 5–6 which consist of carbon atoms and one or 2 oxygen atoms, examples of such ethers being tetrahydrofuran and dioxane.

The acyclic ethers consist of 2 to 8 carbon atoms and are liquid, possible examples being diethyl ether, diisobutyl ether, methyl tert-butyl ether and diisopropyl ether.

Possible saturated hydrocarbons are unbranched and branched hydrocarbons which consist of 5 to 10 carbon atoms and are liquid, possible examples being pentane, hexane, heptane and cyclohexane.

Examples of possible aromatic hydrocarbons are benzene and alkyl-substituted benzenes, the alkyl substituents consisting of 1 to 5 carbon atoms.

Possible basic substances both for the reaction of the phosphorus oxychloride with the long-chain alcohol and for the subsequent conversion to the phosphoric acid diester are amines, for example aliphatic amines of the formula $NR_1R_2R_3$, $R_1$, $R_2$ and $R_3$ being identical or different and being hydrogen or $C_1$–$C_6$-alkyl, or else aromatic amines such as pyridine, picoline and quinoline. The basic substance required for the conversion to the phosphoric acid diester can be added simultaneously with or before the amino alcohol or ammonium alcohol salt.

A solvent is necessary in every case for the second reaction, i.e., if the first reaction step is carried out without a particular solvent, one must now be added. The molar ratio of phosphorus oxychloride to the long-chain alcohol is for example between 1.5:1 and 0.8:1.

The amino alcohol or the ammonium alcohol salt is for example used in excess, based on the long-chain alcohol (about 1.1–1.5 molar excess).

If the reaction of the phosphorus oxychloride with the long-chain alcohol is carried out in the presence of a basic substance, the amount of the basic substance is for example 1 to 3 mol, based on 1 mol of $POCl_3$. The amount of basic substance used for the subsequent conversion to the phosphoric acid diester is for example 1 to 5 mol, based on 1 mol.

The temperature of the reaction of phosphorus oxychloride with the long-chain alcohol is between −30° C. and +30° C., preferably between −15° C. and +5° C. and especially between −10° C. and −5° C.

The duration of this reaction is for example 0.5–5 hours, preferably 1–3 hours and especially 1.5–2 hours. If it is carried out in the presence of a basic substance, the reaction generally proceeds rapidly (about 30 minutes).

The amino alcohol or the ammonium alcohol salt is then added in portions or all at once. Possible ammonium alcohol salts are those with mineral acids (for example sulphuric acid, hydrochloric acid) and also those with organic acids, for example acetic acid, paratoluene-sulphonic acid and the like. This reaction step takes place in an inert solvent. Possible solvents for this step are the same ones as those used for the reaction of the phosphorus oxychloride with the long-chain alcohol, in the case where this reaction is carried out in a solvent.

The basic substance is then added dropwise, either dissolved in one of the indicated solvents or without a solvent. The following are preferably used as solvents for the basic substance: halogenated hydrocarbons, saturated cyclic ethers, acyclic ethers, saturated hydrocarbons having 5 to 10 carbon atoms, liquid aromatic hydrocarbons or mixtures of the above-mentioned solvents.

These are the same solvents as those which can be used for the reaction of the phosphorus oxychloride with the long-chain alcohol.

The addition of the basic substance raises the temperature. Care is taken to ensure that the temperature is kept in a range of between 0° C. and 40° C., preferably between 10° C. and 30° C. and especially between 15° C. and 20° C.

The reaction mixture is then stirred at 5° C. to 30° C., preferably 15° C. to 25° C. (for example for 1 hour to 40 hours, preferably 3 hours to 15 hours).

The reaction mixture is hydrolyzed by the addition of water, during which the temperature should be kept at between 10° C. and 30° C., preferably between 15° C. and 30° C. and especially between 15° C. and 20° C.

The above-mentioned hydrolyzing liquids can also contain basic substances, such basic substances possibly being alkali metal and alkaline earth metal carbonates and bicarbonates.

To complete the hydrolysis, stirring is then continued for a further 0.5 hour to 4 hours, preferably 1 to 3 hours and especially 1.5 to 2.5 hours, at 10° C. to 30° C., preferably at 15° C. to 25° C. and especially at 18° C. to 22° C.

The reaction solution is then washed with a mixture of water and alcohols (preferably saturated aliphatic alcohols having 1 to 4 carbon atoms) which can optionally also contain a basic substance. The mixing ratio water:alcohol can be for example between 5 and 0.5, preferably 1–3 (v/v).

Examples of possible basic substances for the washing liquid are alkali metal and alkaline earth metal carbonates and bicarbonates, as well as ammonia (for example aqueous ammonia). A 3% solution of sodium carbonate in water is particularly preferred.

The reaction solution can then optionally be washed with an acid solution. The acid washing is advantageous for removing basic components of the reaction solution which have not yet reacted, especially when methylene chloride is used as the solvent.

The washing solution consists of a mixture of water and alcohols. Mixtures of saturated aliphatic alcohols having 1 to 4 carbon atoms are preferred, it optionally being possible for an acid substance to be present as well. The mixing ratio water:alcohol can be for example between 5 and 0.5, preferably 1–3 (v/v).

Examples of possible acid substances for the washing liquid are mineral acids and organic acids, for example hydrochloric acid, sulphuric acid, tartaric acid or citric acid. A 10% solution of hydrochloric acid in water is particularly preferred.

This is followed by a further washing with a mixture of water and alcohols. Mixtures of saturated aliphatic alcohols having 1 to 4 carbon atoms are preferred, it optionally being possible for a basic substance to be present as well. The mixing ratio water:alcohol can be for example between 5 and 0.5, preferably 1–3.

The washed phases are then combined and dried in conventional manner, after which the solvent is removed (preferably under reduced pressure, for example at 5 to 100 mbar), optionally after the addition of 150–1000 ml, preferably 300–700 ml and especially 450–550 ml of an aliphatic alcohol (based on 1 molar part by weight of dry product). Preferred alcohols are saturated aliphatic alcohols with a chain length of 1 to 5 carbon atoms, particularly preferred alcohols being n-butanol and isopropanol. The purpose of this alcohol treatment is the complete removal of residual water and the avoidance of foaming.

Further purification of the product can be effected for example by dissolving the crude product in hot ethanol, filtering off the residue and treating the filtrate with a mixed bed ion exchanger such as, for example, Amberlite MB3 in ethanolic solution. Any commercially available acid and basic ion exchangers can be used, simultaneously or successively, instead of a mixed bed ion exchanger.

The solution is then recrystallized from ketones such as, for example, acetone or methyl ethyl ketone; digestion with the above solvents is sufficient in some cases. It may be convenient to purify the products by column chromatography or flash chromatography on silica gel using mixtures of chloroform, methylene chloride, methanol and 25% ammonia solution, for example, as the eluent.

Process variant B consists in the subsequent alkylation of products which are obtainable by process A using amino alcohols. Examples of alkylating agents which can be used are methyl p-toluenesulphonate or dimethyl sulphate. Possible solvents are those which have been mentioned above.

Alkali metal carbonates are examples of basic substances used. The reaction is carried out at elevated temperature, for example at the boiling point of the solvents.

DETAILED DESCRIPTION OF PREFERRED EMBODIMENTS

Figure 1:
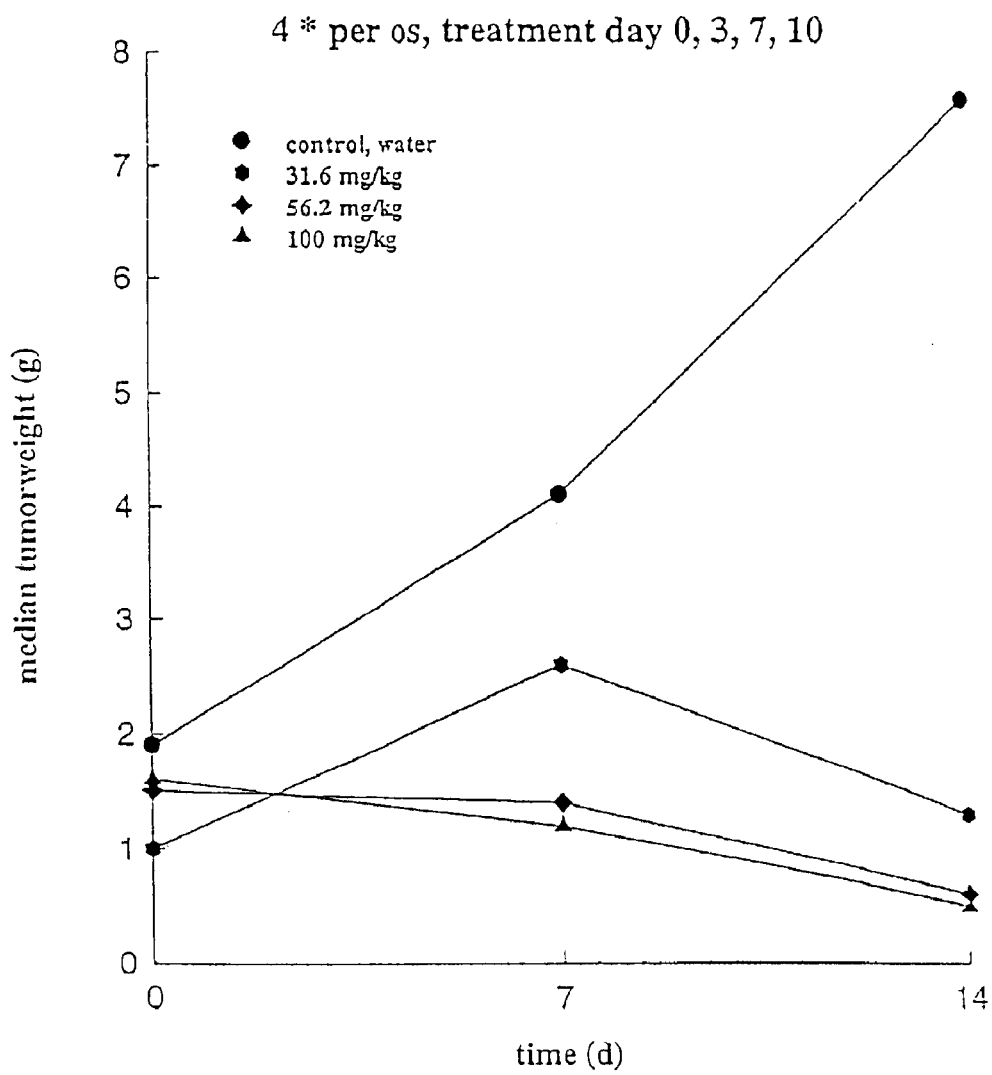
FIG. 1 illustrates Example 1 in the DMBA induced tumor-model, 4*per os, treatment day 0, 3, 7, 10.
Figure 2:
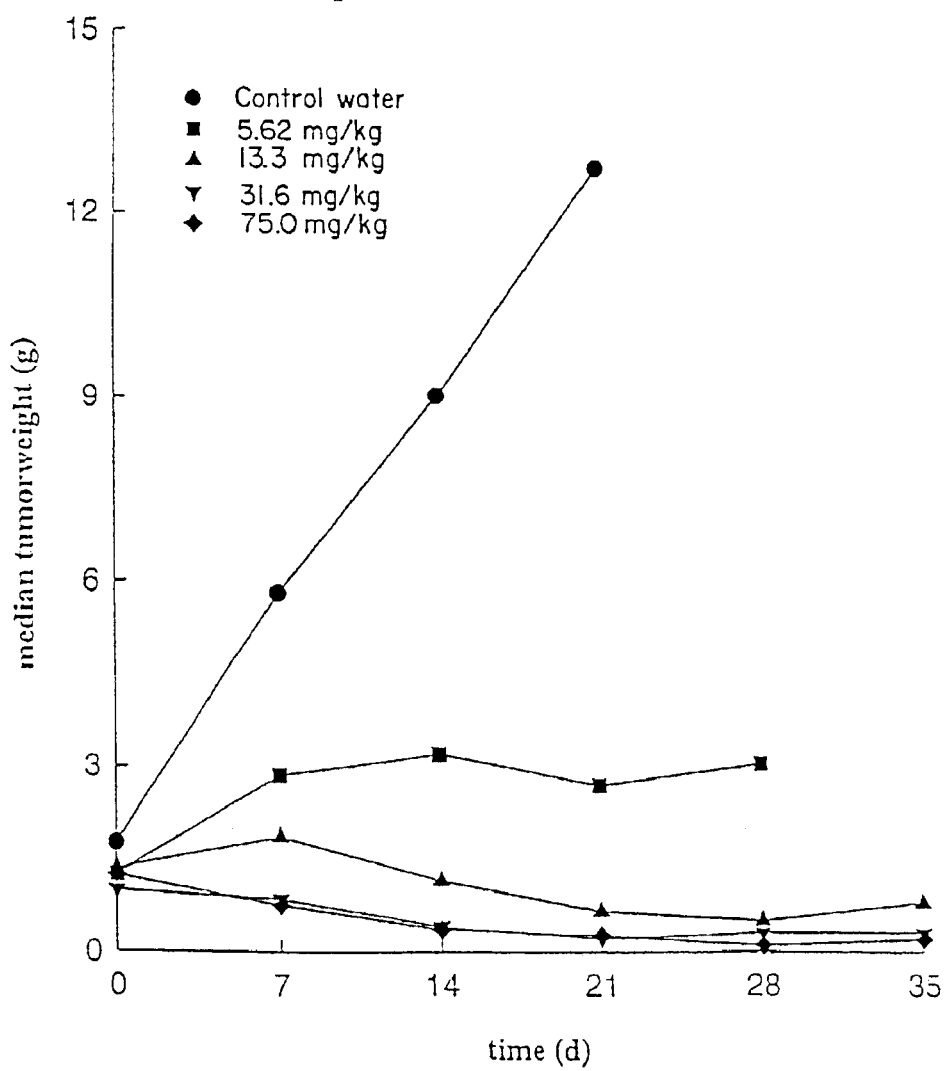
FIG. 2 illustrates Example 1 in the DMBA induced tumor-model, 14*per os, treatment day 0–13.
Figure 3:
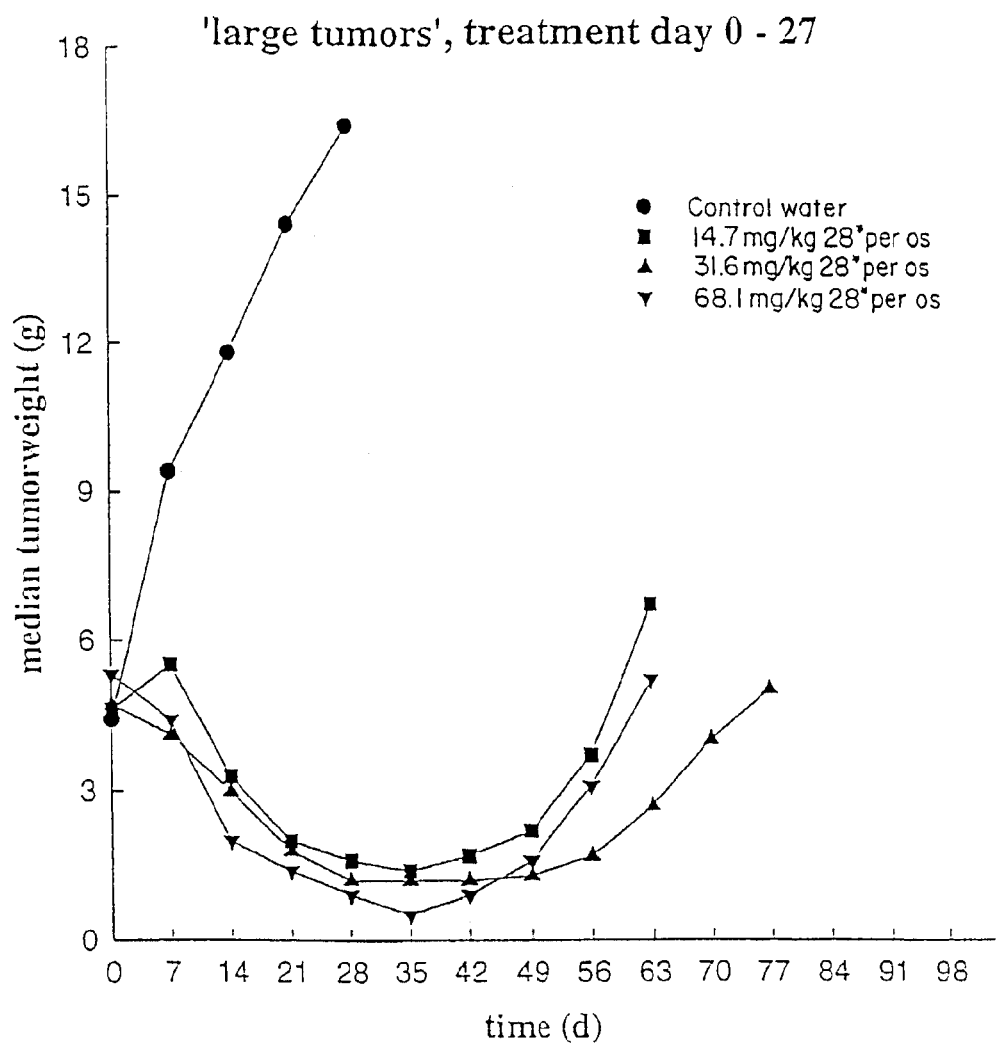
FIG. 3 illustrates Example 1 in the DMBA induced tumor-model, 'large tumors', treatment day 0–27.
Figure 4:
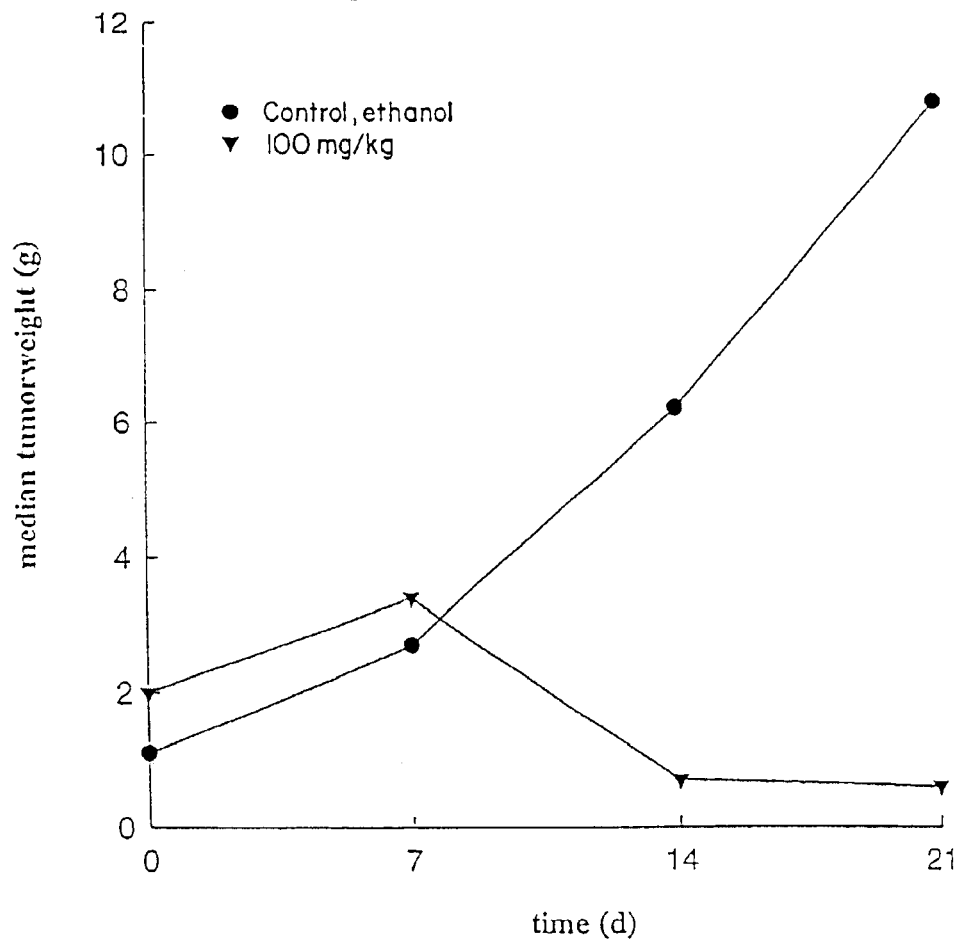
FIG. 4 illustrates Example 8 in the DMBA induced tumor-model, 4*per os, treatment day 0, 3, 7, 10.
Figure 5:
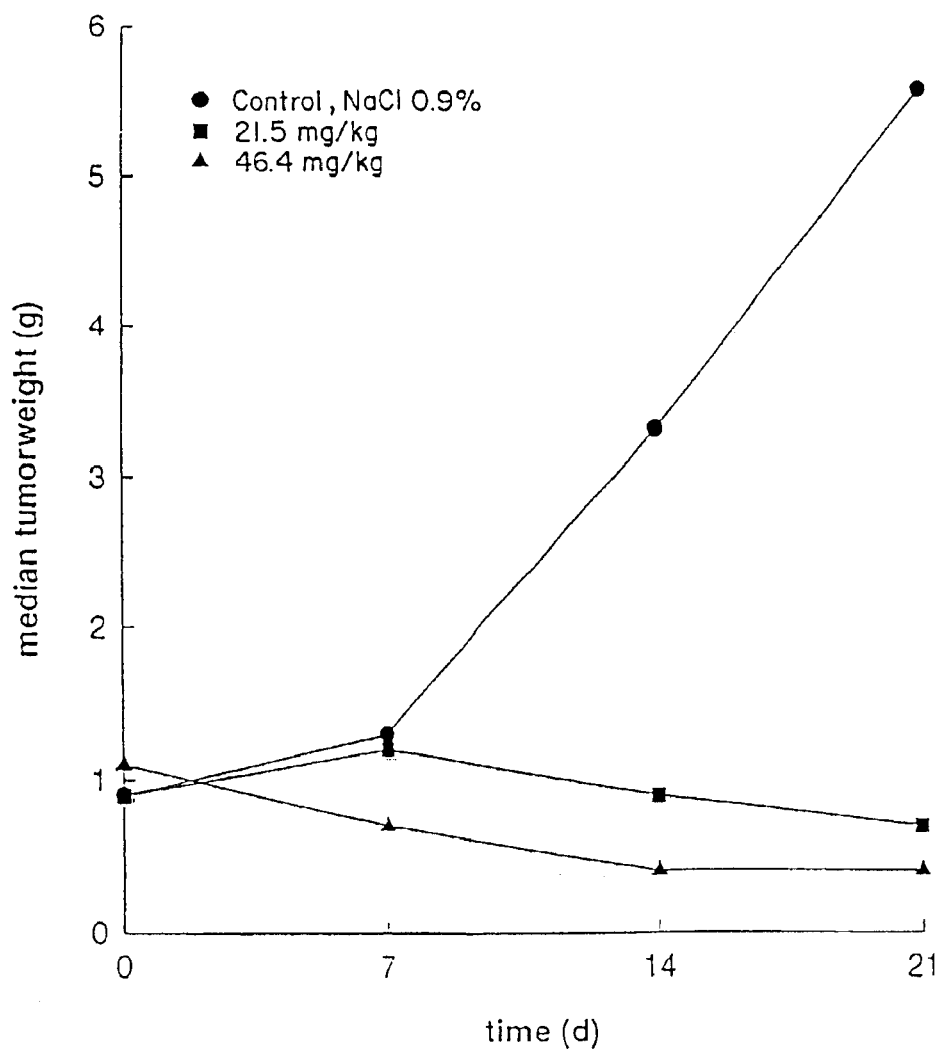
FIG. 5 illustrates Example 13 in the DMBA induced tumor-model, 14*per os, treatment day 0–13.
Figure 6:
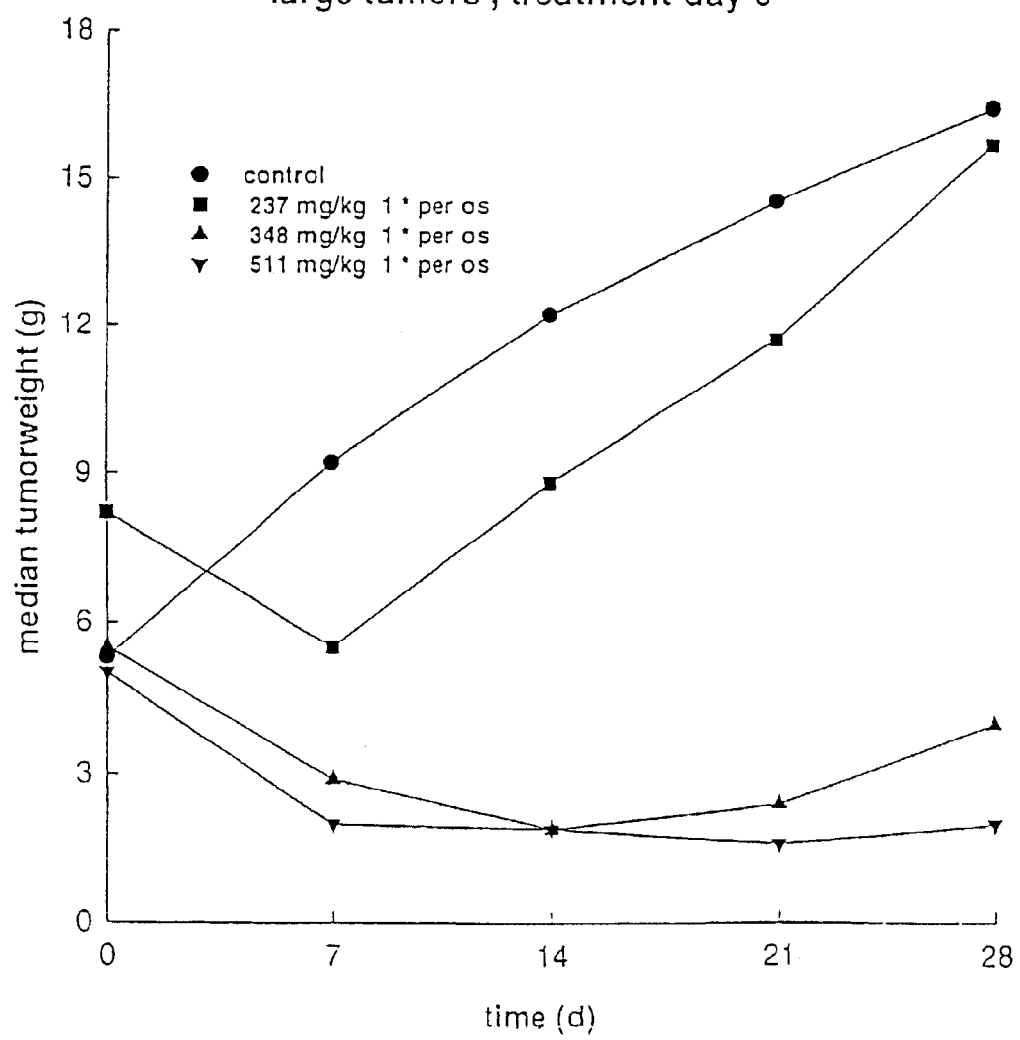
FIG. 6 illustrates Example 13 in the DMBA induced tumor-model, 'large tumors', treatment day 0.
Figure 7:
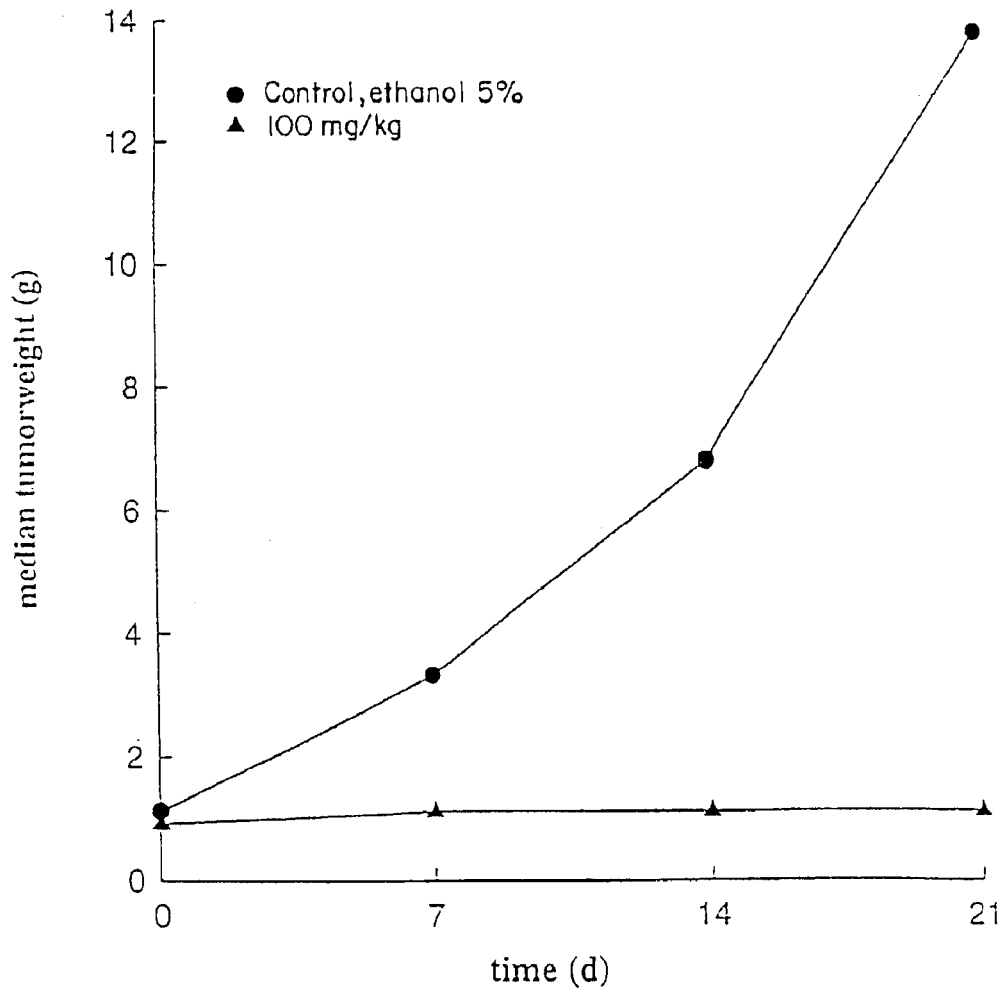
FIG. 7 illustrates Example 20 in the DMBA induced tumor-model, 4*per os, treatment day 0, 3, 7, 10.
Figure 8:
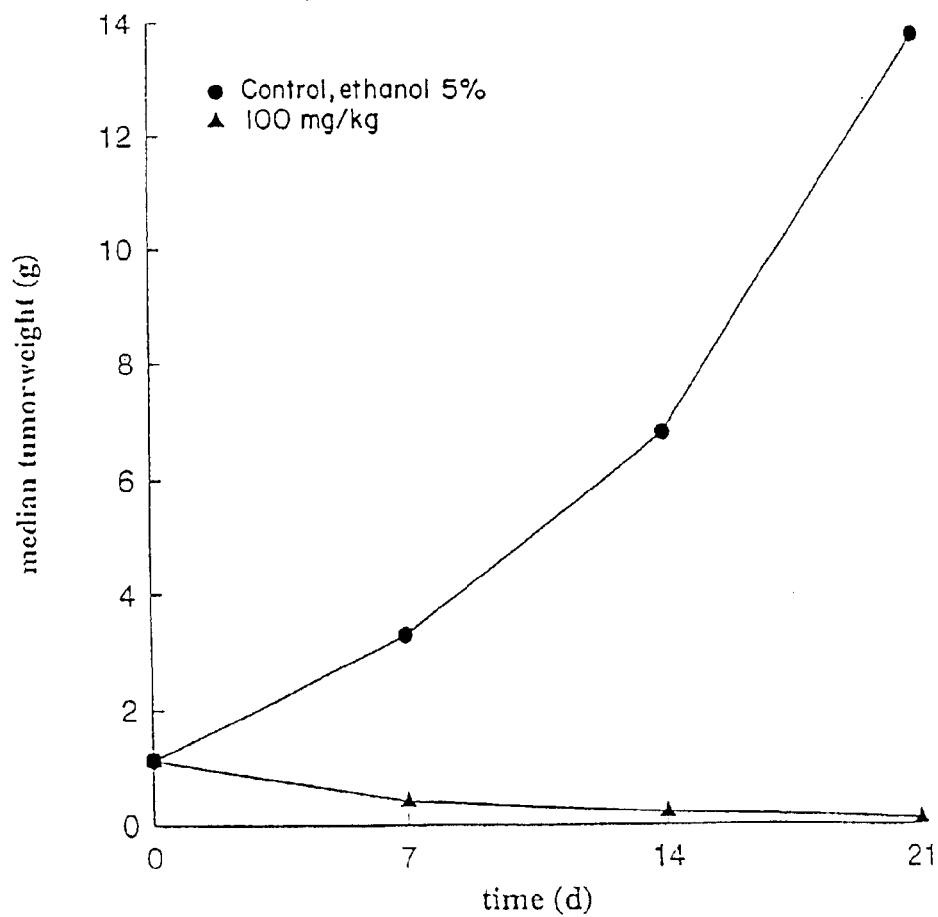
FIG. 8 illustrates Example 21 in the DMBA induced tumor-model, 4*per os, treatment day 0, 3, 7, 10.
Figure 9:
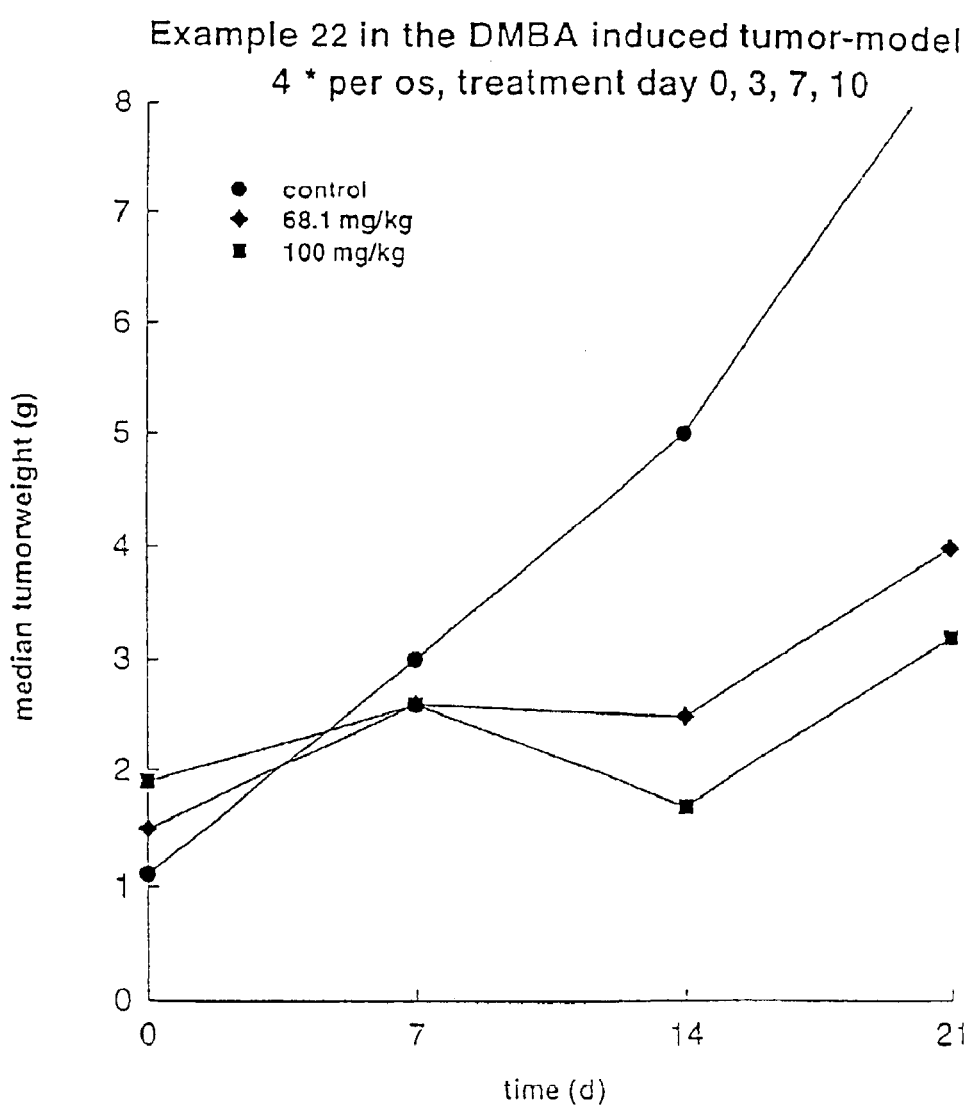
FIG. 9 illustrates Example 22 in the DMBA induced tumor-model, 4*per os, treatment day 0, 3, 7, 10.
Figure 10:
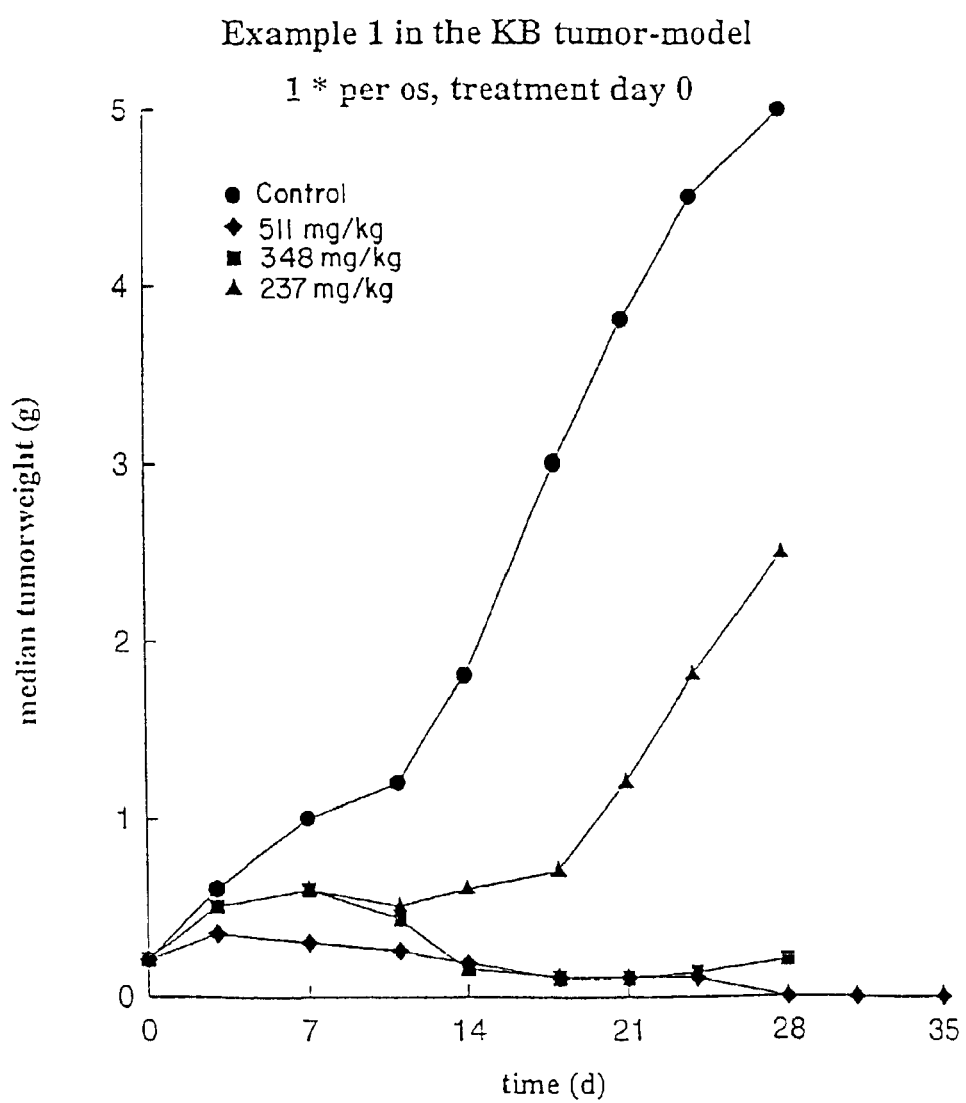
FIG. 10 illustrates Example 1 in the KB tumor-model, 1*per os, treatment day 0.
Figure 11:
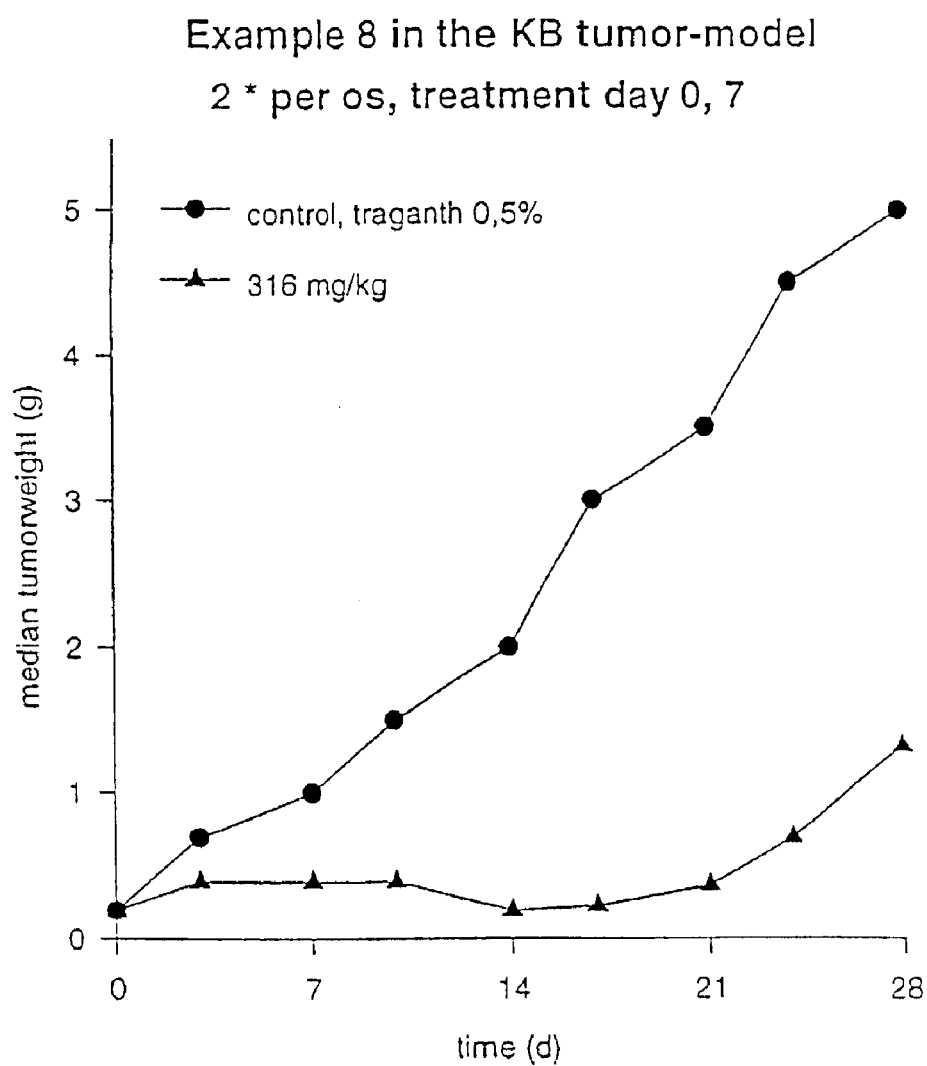
FIG. 11 illustrates Example 8 in the KB tumor-model, 2*per os, treatment day 0, 7.
Figure 12:
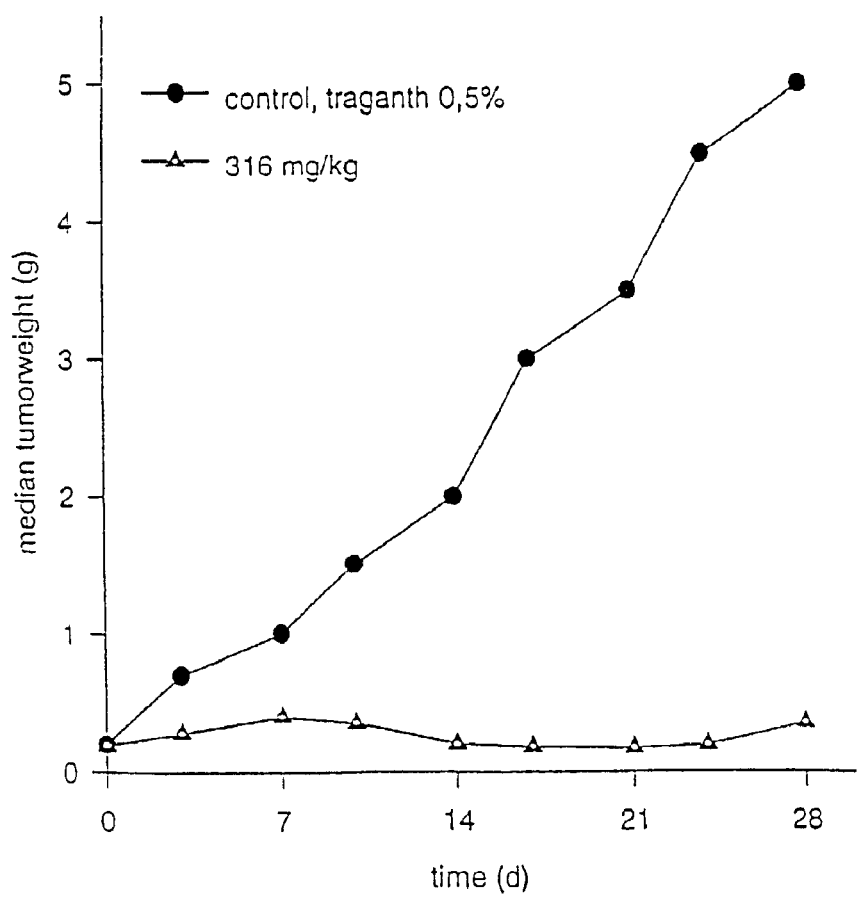
FIG. 12 illustrates Example 10 in the KB tumor-model, 2*per os, treatment day 0, 7.
Figure 13:
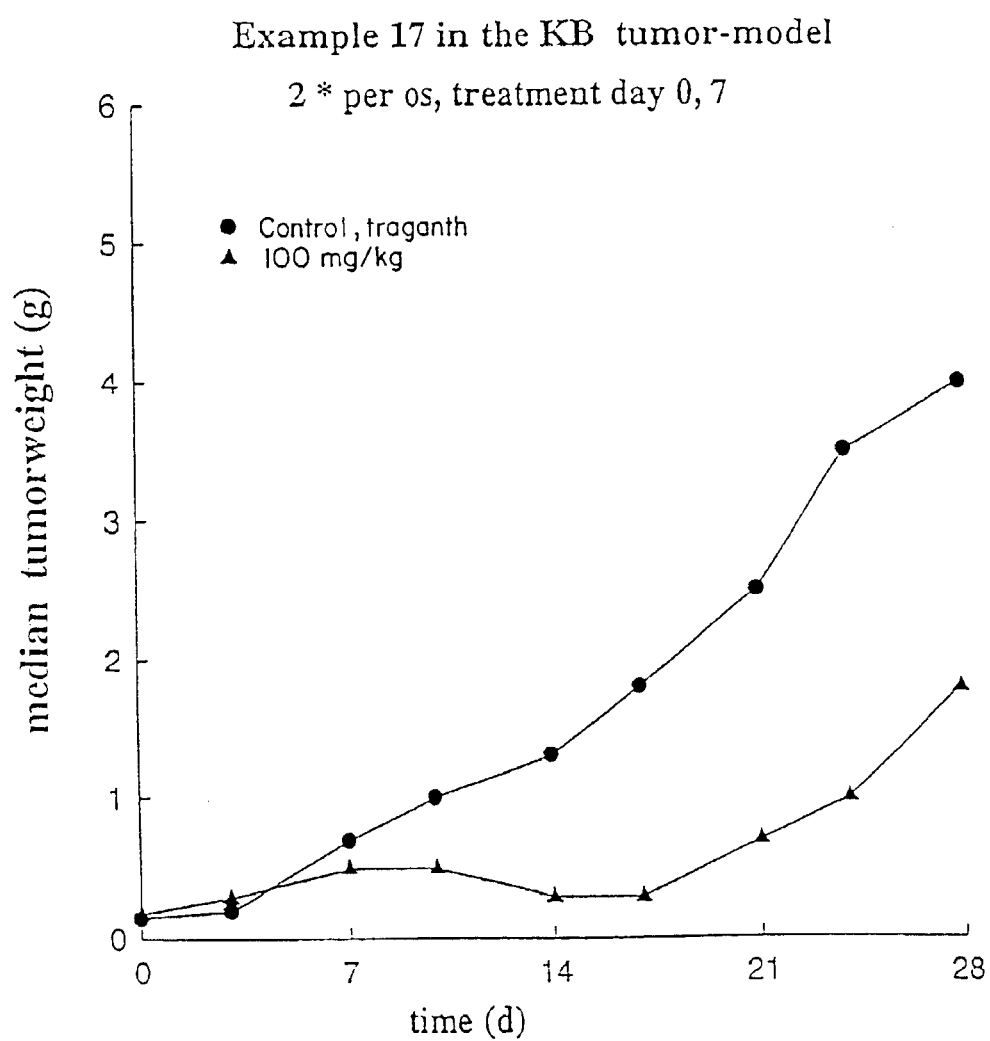
FIG. 13 illustrates Example 17 in the KB tumor-model, 2*per os, treatment day 0, 7.
Figure 14:
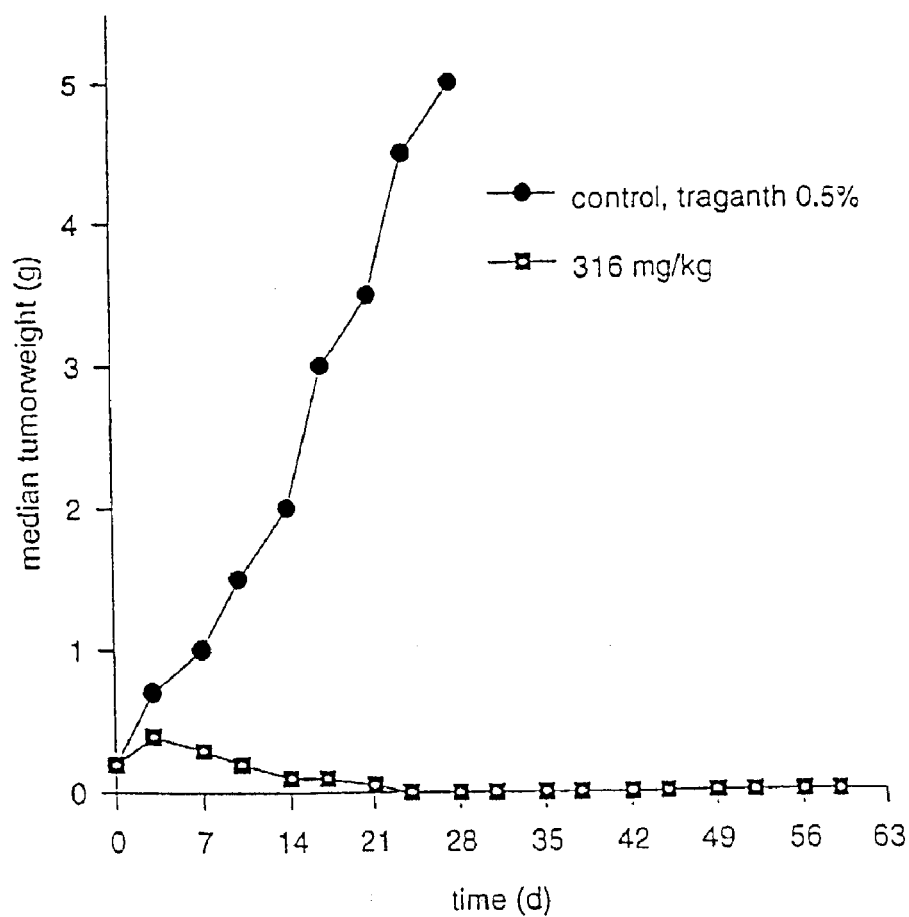
FIG. 14 illustrates Example 21 in the KB tumor-model, 2*per os, treatment day 0, 7.
Figure 15:
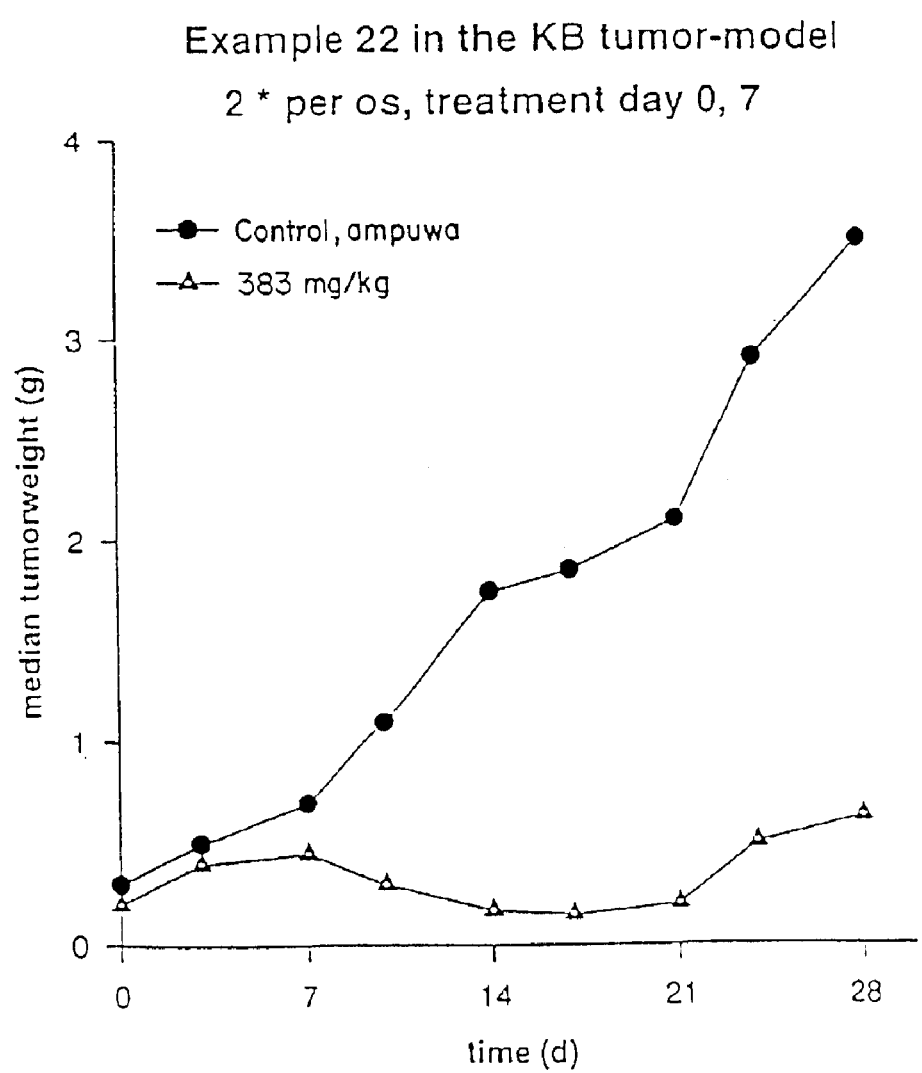
FIG. 15 illustrates Example 22 in the KB tumor-model, 2*per os, treatment day 0, 7.
Figure 16:
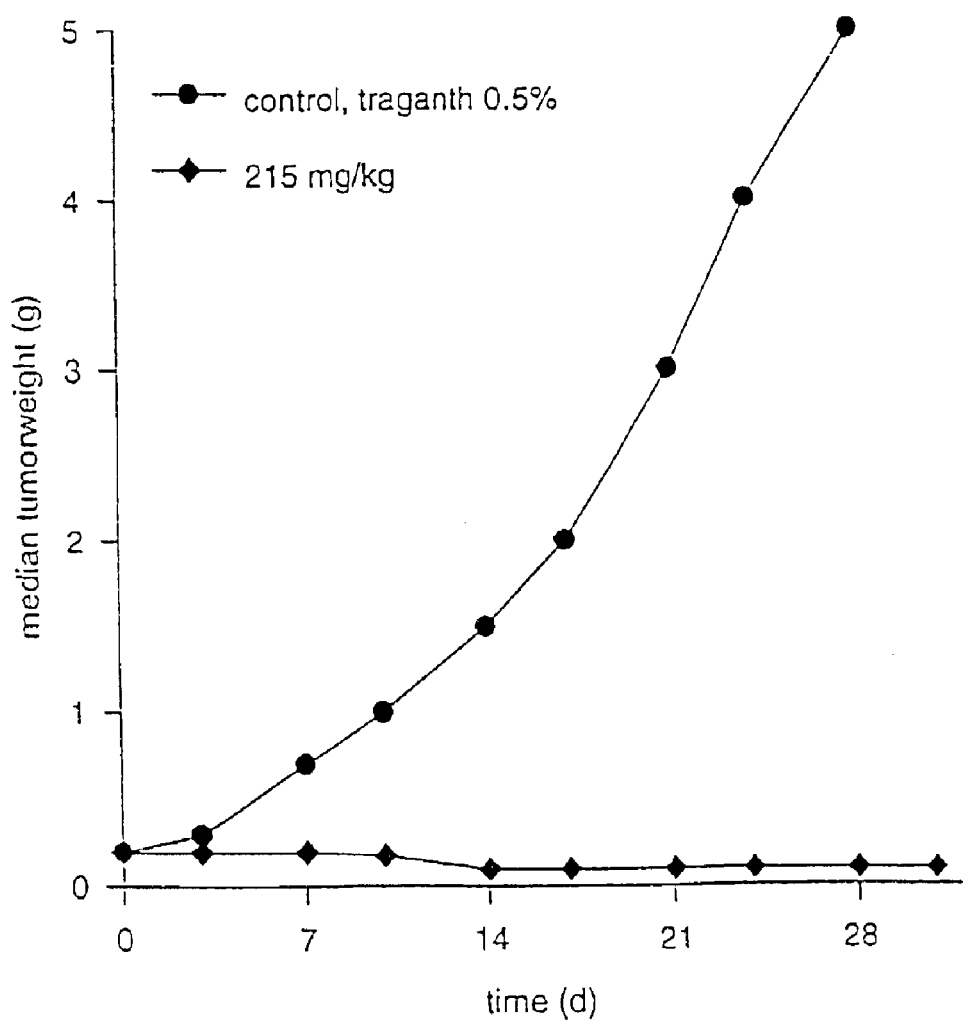
FIG. 16 illustrates Example 24 in the KB tumor-model, 2*per os, treatment day 0, 7.
Figure 17:
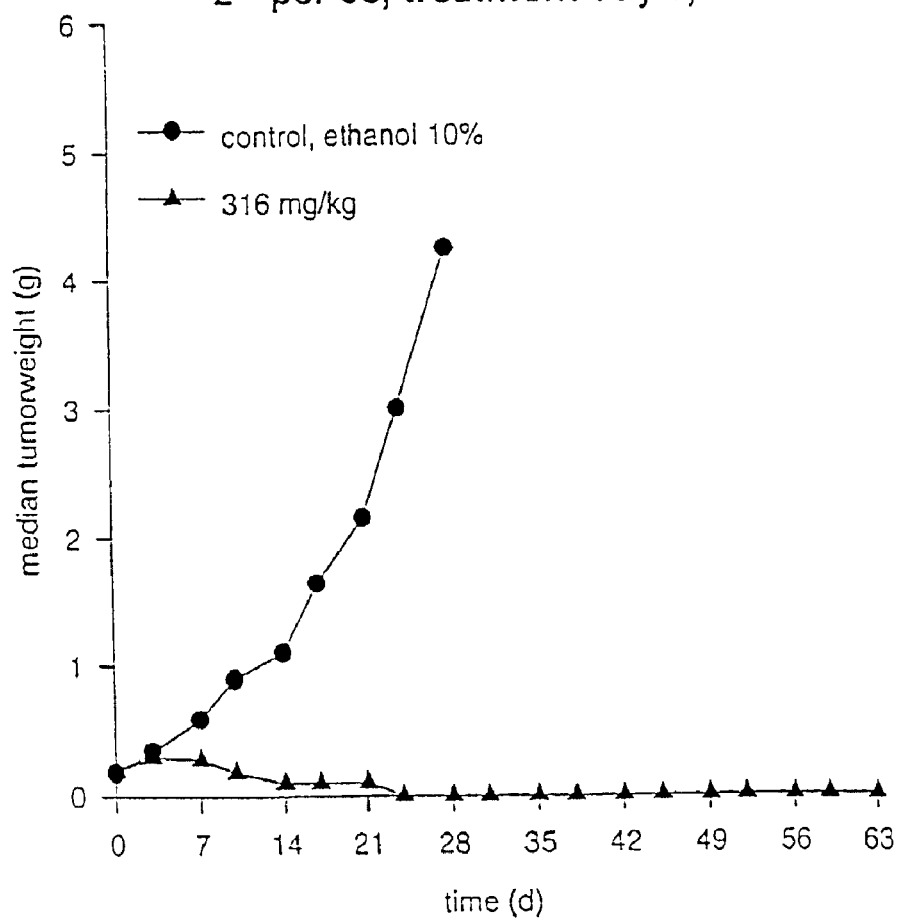
FIG. 17 illustrates Example 25 in the KB tumor-model, 2*per os, treatment day 0, 7.

The following examples illustrate the invention.

EXAMPLES

Example 1

Name (IUPAC Nomenclature)

4-(((Octadecyloxy)hydroxyphosphenyl)oxy)-1,1-dimethylpiperidinium hydroxide internal salt
Abbreviated Name: Octadecyl 1,1-dimethylpiperidinio-4-yl phosphate $C_{25}H_{52}NO_4P$ (461.66).½$H_2O$ Preparation Variant A:

10.3 ml (0.11 mol) of phosphorus oxychloride are placed in 100 ml of chloroform and cooled to 5–10° C. A solution of 27.0 g (0.10 mol) of 1-octadecanol in 100 ml of chloroform and 35 ml of pyridine is added dropwise over 30 min, with stirring. After subsequent stirring for 30 min at 5–10° C., 39.1 g (0.13 mol) of 4-hydroxy-1,1-dimethylpiperidinium tosylate are added in a single portion. After the addition of 40 ml of pyridine and 30 ml of DMF, the mixture is stirred for 24 hours at room temperature. It is then hydrolyzed with 15 ml of water and subsequently stirred for 30 min and the organic phase is washed with 200 ml each of water/methanol (1:1), 3% $Na_2CO_3$/methanol (1:1) and finally water/methanol (1:1). The organic phase is concentrated, the residue is dissolved in 300 ml of hot ethanol and the solution is filtered after cooling. The filtrate is stirred with 80 g of Amberlite MB3 ion exchanger, the mixture is filtered and the filtrate is concentrated. The residue is recrystallized from 300 ml of methyl ethyl ketone, filtered off with suction and dried under vacuum over $P_2O_5$.

Yield: 4.71 g (10%) Elemental analysis:

|  | C | H | N |
|---|---|---|---|
| calc.: | 65.26% | 11.63% | 2.62% |
| found: | 64.38% | 11.61% | 2.73% |
|  | 65.04% | 11.80% | 2.78% |

Thin layer chromatogram: (chloroform/methanol/1 M sodium acetate in 25% ammonia 70:40:10) Rf=0.17 (1-butanol/glacial acetic acid/water 40:10:10) Rf=0.12
Melting point: 270–271° C. (decomposition)

Preparation Variant B:

20.1 ml (0.22 mol) of phosphorus oxychloride are placed in 100 ml of methylene chloride and cooled to 5–10° C. and a solution of 54.1 g (0.20 mol) of octadecanol in 400 ml of methylene chloride and 70.5 ml of pyridine is added over 30 min, with stirring. After subsequent stirring for one hour, 29.9 g (0.26 mol) of 4-hydroxy-1-methylpiperidine in 80 ml of pyridine are added dropwise. After stirring for 3 hours at 10° C., the mixture is hydrolyzed with 30 ml of water while being cooled with ice and is subsequently stirred for one hour. The organic phase is washed with 200 ml each of water/methanol (1:1), 3 percent hydrochloric acid/methanol (1:1) and water/methanol (1:1). The organic phase is dried over $Na_2SO_4$ and concentrated until turbidity appears, and 1 liter of methyl ethyl ketone is added. The crystals are recrystallized from 1 liter of methyl ethyl ketone, filtered off with suction and dried under vacuum over $P_2O_5$.

Yield: 54.1 g (60%) of octadecyl 1-methylpiperidinio-4-yl phosphate 98.1 g (0.22 mol) of octadecyl 1-methylpiperidinio-4-yl phosphate are suspended in 500 ml of absolute ethanol and heated to boiling. Under reflux, a total of 71.8 g (0.39 mol) of methyl p-toluenesulphonate and 26.5 g (0.19 mol) of potassium carbonate are added alternately in eight portions over 2 hours. When the addition is complete, the mixture is refluxed for a further hour. After cooling, it is filtered, the filtrate is concentrated to half and 150 g of moist Amberlite MB3 ion exchanger are added to the solution. After stirring for two hours, the mixture is filtered with suction over kieselguhr/activated charcoal and the filtrate is concentrated and crystallized with acetone. The crystal cake is recrystallized from methyl ethyl ketone and dried under vacuum over $P_2O_5$.

Yield: 46.1 g (46%) of octadecyl 1,1-dimethylpiperidinio-4-yl phosphate Elemental analysis:

|  | C | H | N |
|---|---|---|---|
| calc:. | 65.26% | 11.63% | 2.62% |
| found: | 65.18% | 11.62% | 2.68% |
|  | 65.07% | 11.71% | 2.70% |

Melting point: 271–272° C. (decomposition)

Example 2

Hexadecyl piperidinio-4-yl phosphate $C_{21}H_{44}NO_4P$ (405.558)

7.1 ml (77 mmol) of phosphorus oxychloride are dissolved in 50 ml of dry tetrahydrofuran and, after cooling to 5–10° C., a solution of 17 g (70 mmol) of hexadecanol and 48 ml of triethylamine in 150 ml of tetrahydrofuran is added dropwise, with stirring. When the addition is complete, the mixture is subsequently stirred for 30 min in an ice bath and then left to warm up to room temperature. 10.1 g (100 mmol) of 4-piperidinol are dissolved in 100 ml of tetrahydrofuran and mixed with 17 ml of triethylamine and the mixture is added dropwise to the reaction solution, with stirring, so that the temperature does not exceed 40° C. When the addition is complete, the mixture is refluxed for one hour. While still hot, the solution is separated from the triethylammonium chloride by filtration and, after cooling, is poured into an ice/2 M hydrochloric acid mixture, with stirring. The product obtained on cooling in a refrigerator is taken up in methylene chloride, dried over $MgSO_4$, concentrated and chromatographed on silica gel with methylene chloride/methanol/25% ammonia (70:30:5). The product fractions are combined and concentrated. After recrystallization from methanol, the product is dried under vacuum over $P_2O_5$.

Yield: 10.0 g (35%) Elemental analysis:

|  | C | H | N |
|---|---|---|---|
| calc.: | 62.19% | 10.94% | 3.45% |
| found: | 65.15% | 11.14% | 3.54% |
|  | 62.41% | 11.19% | 3.34% |

Thin layer chromatogram: (chloroform/methanol/25% ammonia 70:20:10) Rf=0.42 (1-butanol/glacial acetic acid/water 40:10:10) Rf=0.33

Example 3

Hexadecyl 1,1-dimethylpiperidinio-4-yl phosphate $C_{25}H_{52}NO_4P$ (461.64).$H_2O$ 5.7 g (14 mmol) of hexadecyl piperidinio-4-yl phosphate are dissolved in 100 ml of methanol and mixed with 11.6 g (84 mmol) of potassium carbonate. 4.0 ml (42 mmol) of dimethyl sulphate are added dropwise over 30 min, with thorough stirring. The mixture is subsequently stirred for 4 hours at 40° C., cooled, filtered and concentrated. The residue is digested with acetone and, after filtration with suction, is dissolved in 100 ml of 96% ethanol. 15 g of Amberlite MB3 ion exchanger are added and the mixture is stirred for 3 hours. After filtration, the filtrate is concentrated and recrystallized twice from methyl ethyl ketone. The crystals are dried under vacuum over $P_2O_5$.

Yield: 3.70 g (61%) Elemental analysis:

|  | C | H | N |
|---|---|---|---|
| calc.: | 61.17% | 11.16% | 3.10% |
| found: | 60.83% | 11.14% | 2.99% |
|  | 60.92% | 11.26% | 3.00% |

Thin layer chromatogram: (chloroform/methanol/25% ammonia 70:20:10) Rf=0.28 (1-butanol/glacial acetic acid/water 40:10:10) Rf=0.13 Melting point: 230° C. (decomposition)

Example 4

Erucyl 1,1-dimethylpiperidinio-4-yl phosphate $C_{29}H_{58}NO_4P$ (515.765).$H_2O$ 10.3 ml (0.11 mol) of phosphorus oxychloride are placed in 50 ml of chloroform, and a solution of 32.5 g (0.10 mol)

of erucyl alcohol (cis-13-docosenyl alcohol) and 32 ml of pyridine in 100 ml of chloroform is added dropwise at 5–10° C. After subsequent stirring for half an hour, 39.1 g (0.13 mol) of 4-hydroxy-1,1-dimethylpiperidinium tosylate are added in a single portion. After the dropwise addition of 40 ml of pyridine, the mixture is left to warm up to room temperature and stirred for 3 hours. It is then hydrolyzed with 15 ml of water, subsequently stirred for half an hour and washed with 100 ml each of water/methanol (1:1), 3% sodium carbonate solution/methanol (1:1), 3% citric acid/methanol (1:1) and water/methanol (1:1). The residue obtained after concentration of the organic phase is digested with acetone and then dissolved in 150 ml of 96% ethanol. This solution is stirred for 3 hours with 20 g of Amberlite MB3 ion exchanger and filtered over kieselguhr to give a clear solution. This is concentrated and chromatographed on silica gel with chloroform/methanol/25% ammonia 70:40:10. The product fractions are combined and concentrated to dryness under vacuum.

Yield: 4.4 g (9%) Elemental analysis:

|  | C | H | N |
|---|---|---|---|
| calc.: | 65.26% | 11.63% | 2.62% |
| found: | 64.38% | 11.61% | 2.73% |
|  | 65.04% | 11.80% | 2.78% |

Thin layer chromatogram: (chloroform/methanol/1 M sodium acetate in 25% ammonia 70:20:10) Rf=0.30

Example 5

Hexadecyl 1,1-dimethylpiperidinio-3-yl phosphate $C_{23}H_{48}NO_4P$ (433.616).$H_2O$ 10.3 ml (0.11 mol) of phosphorus oxychloride are placed in 50 ml of chloroform and cooled to 0–10° C. 24.2 g (0.10 mol) of n-hexadecanol are dissolved in 100 ml of chloroform, 32 ml of pyridine are added and the mixture is added dropwise to the phosphorus oxychloride solution over one hour, with ice cooling. After subsequent stirring for half an hour, 39.2 g (0.13 mol) of 3-hydroxy-1,1-dimethylpiperidinium tosylate are added in a single portion and 40 ml of pyridine are added dropwise over 15 min at room temperature. After stirring for 16 hours at room temperature, the mixture is hydrolyzed with 15 ml of water, stirred for half an hour and washed with 100 ml each of water/methanol (1:1), 3% sodium carbonate solution/methanol (1:1), 3% citric acid/methanol (1:1) and water/methanol (1:1).

The organic phase is dried over sodium sulphate and concentrated. The residue is dissolved in 150 ml of 96% ethanol, the solution is filtered and the filtrate is stirred with Amberlite MB3 ion exchanger. After the ion exchanger has been filtered off, the filtrate is concentrated and the residue is crystallized with acetone, filtered off with suction and dried under vacuum over P2O5.

Yield: 13.5 g (31%) Elemental analysis:

|  | C | H | N |
|---|---|---|---|
| calc.: | 61.17% | 11.16% | 3.10% |
| found: | 60.78% | 11.41% | 2.87% |
|  | 60.85% | 11.31% | 2.86% |

Thin layer chromatogram: (chloroform/methanol/1 M sodium acetate in 25% ammonia 70:40:10) Rf=0.37

Example 6

Octadecyl 1,1-dimethylpiperidinio-3-yl phosphate $C_{25}H_{52}NO_4P$ (461.670).½$H_2O$ This compound is prepared in a manner analgous to Example 5 from 10.3 ml (0.11 mol) of phosphorus oxychloride, 27.0 g (0.10 mol) of octadecanol, 32+40 ml of pyridine and 39.2 g (0.13 mol) of 3-hydroxy-1,1-dimethylpiperidinium tosylate.

Yield: 18.7 g (40%) Elemental analysis:

|  | C | H | N |
|---|---|---|---|
| calc.: | 63.80% | 11.35% | 2.98% |
| found: | 63.38% | 11.72% | 2.63% |
|  | 63.61% | 11.98% | 2.61% |

Thin layer chromatogram: (chloroform/methanol/1 M sodium acetate in 25% ammonia 70:40:10) Rf=0.35

Example 7

Hexadecyl (1,1-dimethylpiperidinio-2-yl) methyl phosphate $C_{24}H_{50}NO_4P$ (447.643).½$H_2O$ This compound is prepared in a manner analogous to Example 5 from 10.3 ml (0.11 mol) of phosphorus oxychloride, 24.2 g (0.10 mol) of hexadecanol, 32+40 ml of pyridine and 41.0 g (0.13 mol) of 2-hydroxymethyl-1,1-dimethylpiperidinium tosylate.

Yield: 22.9 g (51%) Elemental analysis:

|  | C | H | N |
|---|---|---|---|
| calc.: | 63.13% | 11.26% | 3.07% |
| found: | 63.69% | 11.73% | 3.04% |
|  | 63.75% | 11.71% | 3.04% |

Thin layer chromatogram: (chloroform/methanol/1 M sodium acetate in 25% ammonia 70:40:10) Rf=0.47

Example 8

Octadecyl (1,1-dimethylpiperidinio-2-yl) methyl phosphate $C_{26}H_{54}NO_4P$ (475.697).½$H_2O$ This compound is prepared in a manner analogous to Example 5 from 10.3 ml (0.11 mol) of phosphorus oxychloride, 27.0 g (0.10 mol) of octadecanol, 32+40 ml of pyridine and 41.0 g (0.13 mol) of 2-hydroxymethyl-1,1-dimethylpiperidinium tosylate.

Yield: 23.9 g (50%) Elemental analysis:

|  | C | H | N |
|---|---|---|---|
| calc.: | 64.43% | 11.44% | 2.89% |
| found: | 64.50% | 11.61% | 2.67% |
|  | 64.11% | 11.49% | 2.77% |

Thin layer chromatogram: (chloroform/methanol/1 M sodium acetate in 25% ammonia 70:40:10) Rf=0.47

Example 9

Hexadecyl (1,1-dimethylpiperidinio-3-yl) methyl phosphate $C_{24}H_{50}NO_4P$ (447.643).1$H_2O$ This compound is prepared in a manner analogously to Example 5 from 10.3 ml (0.11 mol) of phosphorus oxychloride, 24.2 g (0.10 mol) of hexadecanol, 32+40 ml of pyridine and 41.0 g (0.13 mol) of 3-hydroxymethyl-1,1-dimethylpiperidinium tosylate.

Yield: 17.2 g (39%) Elemental analysis:

|  | C | H | N |
|---|---|---|---|
| calc.: | 61.91% | 11.26% | 3.01% |
| found: | 62.32% | 12.21% | 2.86% |
|  | 61.79% | 11.96% | 2.98% |

Thin layer chromatogram: (chloroform/methanol/1 M sodium acetate in 25% ammonia 70:40:10) Rf=0.29

Example 10

Octadecyl (1,1-dimethylpiperidinio-3-yl) methyl phosphate $C_{26}H_{54}NO_4P$ (475.697).$H_2O$ This compound is prepared in a manner analogous to Example 5 from 10.3 ml (0.11 mol) of phosphorus oxychloride, 27.0 g (0.10 mol) of octadecanol, 32+40 ml of pyridine and 41.0 g (0.13 mol) of 3-hydroxymethyl-1,1-dimethylpiperidinium tosylate.

Yield: 16.7 g (35%) Elemental analysis:

|  | C | H | N |
|---|---|---|---|
| calc.: | 63.25% | 11.43% | 2.84% |
| found: | 62.98% | 12.21% | 2.76% |
|  | 63.67% | 12.47% | 2.80% |

Thin layer chromatogram: (chloroform/methanol/1 M sodium acetate in 25% ammonia 70:40:10) Rf=0.30

Example 11

Tetradecyl 1,1-dimethylhexahydroazepinio-4-yl phosphate $C_{22}H_{46}NO_4P$ (419.54).$H_2O$ This compound is prepared in a manner analogous to Example 5 from 9.6 g (45 mmol) of tetradecanol, 4.6 ml (50 mmol) of phosphorus oxychloride, 10+20 ml of pyridine and 21.3 g (67.5 mmol) of hydroxy-1,1-dimethylhexahydroazepinium tosylate. It is purified by flash chromatography on silica gel with methylene chloride/methanol/25% ammonia 70:40:10.

Yield: 2.70 g (15%) Elemental analysis:

|  | C | H | N |
|---|---|---|---|
| calc.: | 60.40% | 11.05% | 3.20% |
| found: | 60.47% | 11.29% | 3.63% |
|  | 60.78% | 11.52% | 3.68% |

Thin layer chromatogram: (chloroform/methanol/1 M sodium acetate in 25% ammonia 70:40:10) Rf=0.30 (1-butanol/glacial acetic acid/water 40:10:10) Rf=0.08

Example 12

Hexadecyl 1,1-dimethylhexahydroazepinio-4-yl phosphate $C_{24}H_{48}NO_4P$ (445.62)

This compound is prepared in a manner analogous to Example 5 from 10.8 g (45 mmol) of hexadecanol, 4.6 ml (50 mmol) of phosphorus oxychloride, 10+20 ml of pyridine and 21.3 g (67.5 mmol) of 4-hydroxy-1,1-dimethylhexahydrotosylate. It is purified by flash chromatography on silica gel with methylene chloride/methanol/25% ammonia 70:30:10.

Yield: 5.0 g (25%) Elemental analysis:

|  | C | H | N |
|---|---|---|---|
| calc.: | 64.69% | 10.86% | 3.14% |
| found: | 63.90% | 11.54% | 3.22% |
|  | 64.08% | 11.59% | 3.24% |

Thin layer chromatogram: (chloroform/methanol/25% ammonia 80:25:5) Rf=0.10 (1-butanol/glacial acetic acid/water 40:10:10) Rf=0.10 Melting point: >250° C. (decomposition)

Example 13

Octadecyl 1,1-dimethylhexahydroazepinio-4-yl phosphate $C_{26}H_{54}NO_4P$ (475.695).½$H_2O$ This compound is prepared in a manner analogous to Example 5 from 12.1 g (45 mmol) of octadecanol, 4.6 ml (50 mmol) of phosphorus oxychloride, 10+20 ml of pyridine and 21.3 g (67.5 mmol) of 4-hydroxy-1,1-dimethylhexahydroazepinium tosylate. It is purified by flash chromatography on silica gel with methylene chloride/methanol/25% ammonia 70:30:10.

Yield: 5.5 g (26%) Elemental analysis:

|  | C | H | N |
|---|---|---|---|
| calc.: | 64.43% | 11.44% | 2.89% |
| found: | 64.54% | 11.64% | 2.82% |
|  | 64.66% | 11.58% | 2.64% |

Thin layer chromatogram: (chloroform/methanol/1 M sodium acetate in 25% ammonia 70:40:10) Rf=0.22 Melting point: >250° C. (decomposition)

Example 14

Cis-$\Delta^9$-octadecenyl 1,1-dimethylhexahydroazepinio-4-yl phosphate $C_{26}H_{52}NO_4P$ (473.679).$H_2O$ This compound is prepared in a manner analogous to Example 5 from 12.1 g (45 mmol) of cis-.9-octadecenol, 4.6 ml (50 mmol) of phosphorus oxychloride, 10+20 ml of pyridine and 21.3 g (67.5 mmol) of 4-hydroxy-1,1-dimethylhexahydroazepinium tosylate. It is purified by flash chromatography on silica gel with methylene chloride/methanol/25% ammonia 70:30:10.

Yield: 4.5 g (21%) Elemental analysis:

|  | C | H | N |
|---|---|---|---|
| calc.: | 63.51% | 11.07% | 2.85% |
| found: | 64.05% | 11.21% | 3.10% |
|  | 63.80% | 11.06% | 3.06% |

Thin layer chromatogram: (chloroform/methanol/25% ammonia 70:40:10) Rf=0.28 (1-butanol/glacial acetic acid/water 40:10:10) Rf=0.10

Example 15

Eicosyl 1,1-dimethylhexahydroazepinio-4-yl phosphate $C_{28}H_{58}NO_4P$ (503.754).$H_2O$ This compound is prepared in a manner analogous to Example 5 from 13.4 g (45 mmol) of eicosanol, 4.6 ml (50 mmol) of phosphorus oxychloride, 10+20 ml of pyridine and 21.3 g (67.5 mmol) of 4-hydroxy-1,1-dimethylhexahydroazepinium tosylate. It is purified by flash chromatography on silica gel with methylene chloride/methanol/25% ammonia 70:30:10.

Yield: 5.7 g (25%) Elemental analysis:

|  | C | H | N |
|---|---|---|---|
| calc.: | 64.46% | 11.59% | 2.68% |
| found: | 63.51% | 11.48% | 2.95% |
|  | 64.00% | 11.79% | 2.91% |

Thin layer chromatogram: (chloroform/methanol/25% ammonia 70:40:10) Rf=0.12

Example 16

Erucyl 1,1-dimethylhexahydroazepinio-4-yl phosphate $C_{30}H_{60}NO_4P$ (529.789).$H_2O$ This compound is prepared in a manner analogous to Example 5 from 16.2 g (50 mmol) of erucyl alcohol, 5.1 ml (55 mmol) of phosphorus oxychloride, 18+30 ml of pyridine and 20.5 g (65 mmol) of 4-hydroxy-1,1-dimethylhexahydroazepinium tosylate. It is purified by flash chromatography on silica gel with methylene chloride/methanol/25% ammonia 70:30:10.

Yield: 4.1 g (15%) Elemental analysis:

|  | C | H | N |
|---|---|---|---|
| calc.: | 65.78% | 11.41% | 2.56% |
| found: | 65.76% | 12.01% | 2.97% |
|  | 65.82% | 11.63% | 2.96% |

Thin layer chromatogram: (chloroform/methanol/1 M sodium acetate in 25% ammonia 70:40:10) Rf=0.30

Example 17

Octadecyl 1,1-dimethylpyrrolidinio-3-yl phosphate $C_{24}H_{50}NO_4P$ (447.643).½$H_2O$ This compound is prepared in a manner analogous to Example 5 from 3.25 g (12 mmol) of octadecanol, 1.21 ml (13 mmol) of phosphorus oxychloride, 3.7+4.8 ml of pyridine and 4.31 g (15 mmol) of hydroxy-1,1-dimethylpyrrolidinium tosylate. The crude product is purified by dissolution in 96% ethanol and treatment with Amberlite MB3 ion exchanger.

Yield: 1.31 g (25%) Elemental analysis:

|  | C | H | N |
|---|---|---|---|
| calc.: | 63.13% | 11.26% | 3.07% |
| found: | 62.99% | 11.28% | 2.80% |
|  | 62.74% | 11.27% | 2.89% |

Thin layer chromatogram: (chloroform/methanol/1 M sodium acetate in 25% ammonia 70:40:10) Rf=0.25

Example 18

Hexadecyl 2-(1,1-dimethylpyrrolidinio-2-yl)ethyl phosphate $C_{24}H_{50}NO_4P$ (447.643).$H_2O$ This compound is prepared in a manner analogous to Example 5 from 9.21 g (38 mmol) of hexadecanol, 3.9 ml (42 mmol) of phosphorus oxychloride, 13+16 ml of pyridine and 15.8 g (50 mmol) of 2-(2-hydroxyethyl)-1,1-dimethylpyrrolidinium tosylate. It is purified by dissolution in 96% ethanol and treatment with Amberlite MB3 ion exchanger.

Yield: 6.0 g (35%) Elemental analysis:

|  | C | H | N |
|---|---|---|---|
| calc.: | 61.91% | 11.26% | 3.01% |
| found: | 61.82% | 11.69% | 3.21% |
|  | 61.93% | 11.86% | 3.28% |

Thin layer chromatogram: (chloroform/methanol/1 M sodium acetate in 25% ammonia 70:40:10) Rf=0.38

Example 19

Octadecyl 2-(1,1-dimethylpyrrolidinio-2-yl)ethyl phosphate $C_{26}H_{54}NO_4P$ (475.697).½$H_2O$ This compound is prepared in a manner analogous to Example 5 from 10.3 g (38 mmol) of octadecanol, 3.9 ml (42 mmol) of phosphorus oxychloride, 13+16 ml of pyridine and 15.8 g (50 mmol) of 2-(2-hydroxyethyl)-1,1-dimethylpyrrolidinium tosylate. It is purified by dissolution in 96% ethanol and treatment with Amberlite MB3 ion exchanger.

Yield: 7.8 g (43%) Elemental analysis:

|  | C | H | N |
|---|---|---|---|
| calc.: | 64.43% | 11.44% | 2.89% |
| found: | 64.69% | 11.77% | 2.64% |
|  | 64.84% | 11.88% | 2.69% |

Thin layer chromatogram: (chloroform/methanol/1 M sodium acetate in 25% ammonia 70:40:10) Rf=0.35

Example 20

Hexadecyl (1,1-dimethylpyrrolidinio-2-yl) methyl phosphate $C_{23}H_{48}NO_4P$ (433.616).½$H_2O$ This compound is prepared in a manner analogous to Example 5 from 9.21 g (38 mmol) of hexadecanol, 3.9 ml (42 mmol) of phosphorus oxychloride, 13+16 ml of pyridine and 15.1 g (50 mmol) of 2-hydroxymethyl-1,1-dimethylpyrrolidinium tosylate. It is purified by dissolution in 96% ethanol and treatment with Amberlite MB3 ion exchanger.

Yield: 8.3 g (51%) Elemental analysis:

|  | C | H | N |
|---|---|---|---|
| calc.: | 62.41% | 11.16% | 3.16% |
| found: | 62.09% | 11.48% | 3.01% |
|  | 62.25% | 11.66% | 3.09% |

Thin layer chromatogram: (chloroform/methanol/1 M sodium acetate in 25% ammonia 70:40:10) Rf=0.33

Example 21

Octadecyl (1,1-dimethylpyrrolidinio-2-yl) methyl phosphate $C_{25}H_{52}NO_4P$ (461.67).½$H_2O$ This compound is prepared in a manner analogous to Example 5 from 10.3 g (38 mmol) of octadecanol, 3.9 ml (42 mmol) of phosphorus oxychloride, 13+16 ml of pyridine and 15.1 g (50 mmol) of 2-hydroxymethyl-1,1-dimethylpyrrolidinium tosylate. It is purified by dissolution in 96% ethanol and treatment with Amberlite MB3 ion exchanger.

Yield: 9.0 g (52%) Elemental analysis:

|  | C | H | N |
|---|---|---|---|
| calc.: | 63.80% | 11.35% | 2.98% |
| found: | 63.13% | 11.57% | 2.84% |
|  | 63.55% | 11.66% | 2.82% |

Thin layer chromatogram: (chloroform/methanol/1 M sodium acetate in 25% ammonia 70:40:10) Rf=0.35

Example 22

Hexadecyl 1-methylquinuclidinio-3-yl phosphate $C_{24}H_{48}NO_4P$ (445.64).1.5 $H_2O$ 2.7 ml (30 mmol) of phosphorus oxychloride are dissolved in 25 ml of chloroform and cooled to 5–10° C. and a solution of 6.4 g (26 mmol) of hexadecanol and 10 ml of pyridine in 50 ml of chloroform is added dropwise over one hour. After subsequent stirring for half an hour at room temperature, a solution of 4.5 g (35 mmol) of 3-hydroxyquinuclidine and 5 ml of pyridine in 10 ml of chloroform is added. After stirring for 5 hours at room temperature, the mixture is hydrolyzed with 15 ml of water and subsequently stirred for half an hour. It is then washed twice with 100 ml of water/methanol (1:1) and the organic phase is dried over magnesium sulphate and concentrated to dryness. The residue is chromatographed on silica gel with methylene chloride/methanol 80:25 and then methylene chloride/methanol/25% ammonia 80:25:5. The product fractions are purified, evaporated to dryness and crystallized with acetone. The crystals are dried under vacuum over $P_2O_5$.

Yield: 4.95 g (44%) of hexadecyl quinuclidinio-3-yl phosphate 4.95 g (11.5 mmol) of hexadecyl quinuclidinio-3-yl phosphate are dissolved in 30 ml of methanol, 13.7 g (69 mmol) of potassium carbonate and 8.5 ml of water are added and a solution of 3.3 ml (35 mmol) of dimethyl sulphate in 5 ml of methanol is added dropwise, with thorough stirring. After stirring for 14 hours at room temperature, the inorganic salts are filtered off, the filtrate is concentrated to dryness and the residue is taken up in methylene chloride. After filtration, the filtrate is chromatographed on silica gel with methylene chloride/methanol/25% ammonia 70:30:5. The product fractions are combined, evaporated to dryness and stirred with acetone until crystallization occurs. The crystals are dried under vacuum over $P_2O_5$.

Yield: 2.7 g (49%) Elemental analysis:

|  | C | H | N |
|---|---|---|---|
| calc.: | 60.99% | 10.88% | 2.96% |
| found: | 61.38% | 11.04% | 3.29% |
|  | 61.46% | 11.22% | 3.25% |

Thin layer chromatogram: (chloroform/methanol/25% ammonia 70:40:10) Rf=0.44

Example 23

Octadecyl 1-methylquinuclidinio-3-yl phosphate $C_{26}H_{52}NO_4P$ (473.68).2$H_2O$ This compound is prepared in a manner analogous to Example 5 from 18.3 g (67.5 mmol) of octadecanol, 7.0 ml (75 mmol) of phosphorus oxychloride, 18+20 ml of pyridine and 28.3 g (90 mmol) of 3-hydroxy-1-methylquinuclidinium tosylate. It is purified by dissolution in 96% ethanol and treatment with Amberlite MB3 ion exchanger.

Yield: 18.4 g (57%) Elemental analysis:

|  | C | H | N |
|---|---|---|---|
| calc.: | 61.27% | 11.07% | 2.75% |
| found: | 61.27% | 10.91% | 2.45% |
|  | 61.95% | 11.23% | 2.51% |

Thin layer chromatogram: (chloroform/methanol/1 M sodium acetate in 25% ammonia 70:40:10) Rf=0.37 (1-butanol/glacial acetic acid/water 40:10:10) Rf=0.13

Example 24

Hexadecyl 1,1-dimethyltropanio-4-yl phosphate $C_{25}H_{50}NO_4P$ (459.654).$H_2O$ This compound is prepared in a manner analogous to Example 5 from 12.1 g (50 mmol) of hexadecanol, 5.1 ml (55 mmol) of phosphorus oxychloride, 17+40 ml of pyridine and 21.3 g (65 mmol) of 4-hydroxy-1,1-dimethyltropanium tosylate. It is purified by dissolution in 96% ethanol, treatment with Amberlite MB3 ion exchanger and recrystallization from acetone.

Yield: 11.3 g (49%) Elemental analysis:

|  | C | H | N |
|---|---|---|---|
| calc.: | 62.86% | 10.97% | 2.93% |
| found: | 62.45% | 11.52% | 2.82% |
|  | 62.58% | 11.52% | 2.75% |

Thin layer chromatogram: (chloroform/methanol/1 M sodium acetate in 25% ammonia 70:40:10) Rf=0.28

Example 25

Octadecyl 1,1-dimethyltropanio-4-yl phosphate $C_{27}H_{54}NO_4P$ (487.708)

This compound is prepared in a manner analogous to Example 5 from 13.5 g (50 mmol) of octadecanol, 5.1 ml (55 mmol) of phosphorus oxychloride, 17+20 ml of pyridine and 21.3 g (65 mmol) of 4-hydroxy-1,1-dimethyltropanium tosylate. It is purified by dissolution in 96% ethanol and treatment with Amberlite MB3 ion exchanger.

Yield: 10.7 g (44%) Elemental analysis:

|  | C | H | N |
|---|---|---|---|
| calc.: | 66.49% | 11.16% | 2.87% |
| found: | 65.72% | 11.48% | 2.64% |
|  | 66.27% | 11.78% | 2.65% |

Thin layer chromatogram: (chloroform/methanol/1 M sodium acetate in 25% ammonia 70:40:10) Rf=0.22

Experiment 1

The inventors induced mammary carcinomas in female Sprague-Dawley rats (Mollegaard Breeding Center, DK-4236 Ejby) aged 50 days by administering a single dose of 20 mg 7,12-dimethylbenz(a)anthracene (DMBA) dissolved in 1 ml of olive oil to each rat by gavage. The first tumor appeared approximately one month after feeding the subject rats with DMBA.

Tumor weights were estimated on the basis of tumor volume. This was accomplished by palpating tumors and comparing the volumes of the palpated tumors with the volumes of prefabricated plasticine models in the manner taught by Druckrey, et al., "Experimentelle Beiträge zum Dosis-Problem in der Krebs-Chemotherapie und zur Wirkungsweise von Endoxan, Dtsch. Med. Wschr., 88:651 (1963). Each of the relevant plasticine models was then weighed and converted to a tumor weight by means of a factor reflecting the relationship between the specific weight of each tumor tissue and its corresponding plasticine model. To ensure the accuracy of this method, the inventors simultaneously estimated the weights of 99 individual tumors by both palpation and direct weighing of extirpated tumors. A statistical evaluation of the resulting data indicated a correlation coefficient of 0.98.

Test rats having a total tumor weight of approximately 1 g were randomly allocated amongst various dosage and control groups, each group having a total of 6–7 rats. In this way, the inventors were able to ensure an approximately equal distribution amongst the experimental groups of tumors having different latencies, total tumor weight and numbers of tumor nodes.

After separating the rats into dosage and control groups, the inventors commenced therapy with the compounds of Examples 1, 8, 13, 20, 21 and 22 of the subject application. Each compound was dissolved in 0.9% NaCl and administered per os (stomach tube) in accordance with the regimen schedules detailed in Graphs 1–9 hereinbelow. The control group was given tap water in accordance with the same schedule.

Following treatment, the test rats were observed for a period of at least 4 days after administration of the last scheduled dose. During the observation period, tumor weights were determined for each of the test rats at regular intervals.

The test rats were all housed under specific pathogen free (SPF) conditions with unrestricted water supply (acidified to pH 3) and standard pellet lab chow (Altromin 1324).

Experiment 2

The inventors used female, nu/nu mice (strain NMRI) aged 9–10 weeks and weighing 21–29 g (Breeder: Bomholtgard Breeding and Research Center, DK-8680 Ry) for testing. Tumor fragments consisting of the human KB tumors (ATCC; Rockville, Md.; cell line ATCC CCL 17 KB, human epidermoid larynx tumors), and having an average diameter of 2 mm, were implanted subcutaneously into the right side of the test mice.

The test mice were randomly assigned to various treatment and control groups.

Tumor weights were estimated by first palpating the tumors and then comparing the volumes of the palpated tumors with the volumes of prefabricated plasticine models according to Druckrey, et al., "Experimentelle Beiträge zum Dosis-Problem in der Krebs-Chemotherapie und zur Wirkungsweise von Endoxan, Dtsch. Med. Wschr., 88:651 (1963). After determining the weight of the models, the inventors converted each of these values to a tumor weight by determining the relationship between the specific weight of each tumor tissue and its corresponding plasticine model. To ensure the accuracy of this method, the inventors simultaneously estimated the weights of 99 individual tumors by both palpation and direct weighing of extirpated tumors. A statistical evaluation of the resulting data indicated a correlation coefficient of 0.98.

Once the KB tumor implants attained a weight of approximately 0.2 g, the inventors commenced therapy with the compounds of Examples 1, 8, 17, 21, 22, 24 and 25 of the subject application. Each compound was dissolved in 0.9% NaCl and administered per os (stomach tube) in accordance with the regimen schedules detailed in Graphs 10–17 hereinbelow. The control mice were treated with the vehicle alone.

The mice were observed for a period of at least 21 days following administration of the last scheduled dose. During the observation period, tumor weights were determined for each of the test mice at regular intervals.

The test mice were all housed under specific pathogen free (SPF) conditions with unrestricted water supply (acidified to pH 3) and standard pellet lab chow (Altromin 1324).

Results of Experiments 1 and 2

Results from Experiments 1 and 2 were calculated and expressed in accordance with the growth inhibition index (GII) described in Voegeli, et al., "Selective cytostatic activity of Hexadecylphosphocholine against tumor cells in vitro leads to the establishment of an in vivo screening system for phospholipid analogues," Int. J. Oncol., 2:161 (1993). The GII values from Experiments 1 and 2 are detailed in Table 1 below.

TABLE 1

| Example Number | Dose (mg/kg) | DMBA (G.I.I. %) | KB (G.I.I. %) |
|---|---|---|---|
| 1 | 1 × 511 |  | 103 |
|  | 4 × 100 | 119 |  |
|  | 14 × 31.6 | 108 |  |
|  | 28 × 68.1 | 137 |  |
| 8 | 4 × 100 | 125 |  |
| 8 | 2 × 316 |  | 100 |
| 10 | 2 × 316 |  | 99 |
| 13 | 1 × 511 | 145 |  |
|  | 14 × 46.4 | 129 |  |
| 17 | 2 × 100 |  | 90 |
| 20 | 4 × 100 | 99 |  |

TABLE 1-continued

| Example Number | Dose (mg/kg) | DMBA (G.I.I. %) | KB (G.I.I. %) |
|---|---|---|---|
| 21 | 4 × 100 | 116 | |
|  | 2 × 316 |  | 106 |
| 22 | 4 × 100 | 105 | |
|  | 2 × 383 |  | 102 |
| 24 | 2 × 215 |  | 108 |
| 25 | 2 × 316 |  | 110 |

G.I.I. = Growth Inhibition Index (>100 = Tumor regression)

BRIEF DESCRIPTION OF THE FIGURES

The data presented in Graphs 1–17 and Table 1 hereinabove demonstrates that when the compounds of Examples 8, 10 and 20 are administered in accordance with specified dosage regimens, it is possible to achieve a reduction in tumor volume below that of initial tumor volume (GII= 100%). It is further demonstrated by this data that when the compounds of Examples 1, 8, 13, 21, 22, 24 and 25 of the subject application are administered in accordance with specified dosage regimens, tumor regression is possible (GII>100%). Finally, this data shows that the compounds of Examples 1, 21 and 25 are capable of effecting tumor remission, leading to a complete disappearance of tumors.

Treating the DMBA-induced mammary carcinomas in test rats and the KB implanted tumors in test mice with standard cytostatics (e.g., Cyclophosphamide, Cisplatin and Adriamycin) proved relatively ineffective. This result demonstrates that the compounds described herein are superior to presently known cytostatics employed clinically in the treatment of tumors.

While the invention has been described in connection with what is presently considered to be the most practical and preferred embodiments, it is understood that the invention is not limited to the disclosed embodiments, but on the contrary is intended to cover various modifications and equivalent arrangements included within the spirit and scope of the appended claims.

Thus, it is to be understood that variations in the compounds and uses thereof can be made without departing from the novel aspects of the invention as defined in the claims.

The present application is a continuation-in-part application of U.S. patent application Ser. No. 08/086,850, filed Jul. 7, 1993, the contents of which are herein incorporated by reference. Additionally, the present application relies for priority upon the inventors' German Application No. P 42 22 910.3, filed Jul. 11, 1992, the contents of which are herein incorporated by reference.

What is claimed is:

1. A method of treating a skin carcinoma which comprises administering to a host having a skin disease an effective amount of a compound formula I.

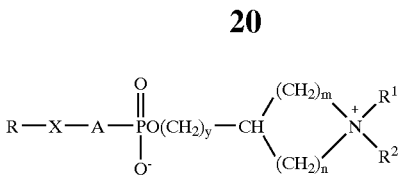

in which

R is a linear or branched alkyl radical having 10 to 24 carbon atoms, which can also contain one to three double or triple bonds;

$R^1$ and $R^2$ independently of each other are hydrogen or a liner, branched or cyclic hydrocarbon radical having 1 to 6 carbon atoms, the hydrocarbon radical being saturated or unsaturated and optionally containing a substituent selected from the group consisting of Cl, OH or $NH_2$, wherein two of the hydrocarbon radicals may be bonded together to from a ring;

A is a single bond or one of the groups of the formula:

 (II)

 (III)

 (IV)

 (V)

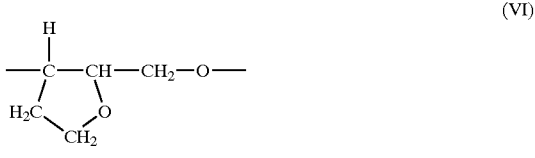 (VI)

in which the groups having formula (II) to (VI) are orientated in such a way that the oxygen atom is bonded to the phosphorus atom of compound (I);

X is an oxygen or sulfur atom or NH when A is a single bond, or an oxygen or sulfur atom when A is one of the groups having formula (II) to (IV);

y is equal to 0 or a natural number between 1 and 3; and m and n independently of one another are 0 or a natural number selected such that the sum of m+n equals 4.

2. The method of claim 1, wherein the skin carcinoma is epidermoid carcinoma.

3. The method of claim 1, wherein the skin carcinoma is human epidermoid carcinoma.

* * * * *